(12) United States Patent
Steele et al.

(10) Patent No.: US 11,406,731 B2
(45) Date of Patent: Aug. 9, 2022

(54) HYGROSCOPIC, CROSSLINKING COATINGS AND BIOADHESIVES

(71) Applicant: NANYANG TECHNOLOGICAL UNIVERSITY, Singapore (SG)

(72) Inventors: Terry W. J. Steele, Singapore (SG); Ivan Djordjevic, Singapore (SG)

(73) Assignee: NANYANG TECHNOLOGICAL UNIVERSITY, Singapore (SG)

(*) Notice: Subject to any disclaimer, the term of this patent is extended or adjusted under 35 U.S.C. 154(b) by 80 days.

(21) Appl. No.: 16/645,394

(22) PCT Filed: Sep. 6, 2018

(86) PCT No.: PCT/SG2018/050452
§ 371 (c)(1),
(2) Date: Mar. 6, 2020

(87) PCT Pub. No.: WO2019/050479
PCT Pub. Date: Mar. 14, 2019

(65) Prior Publication Data
US 2020/0282102 A1 Sep. 10, 2020

(30) Foreign Application Priority Data
Sep. 6, 2017 (SG) .......................... 10201707244R

(51) Int. Cl.
| A61L 24/04 | (2006.01) |
| A61L 24/00 | (2006.01) |
| A61L 24/02 | (2006.01) |
| C08G 83/00 | (2006.01) |
| C08L 101/00 | (2006.01) |
| C09J 201/00 | (2006.01) |

(52) U.S. Cl.
CPC ......... *A61L 24/046* (2013.01); *A61L 24/0015* (2013.01); *A61L 24/02* (2013.01); *C08G 83/004* (2013.01); *C08L 101/005* (2013.01); *C09J 201/005* (2013.01)

(58) Field of Classification Search
CPC .... A61L 21/046; A61L 24/0015; A61L 24/02; C08G 83/004; C08L 101/005; C09J 201/005
See application file for complete search history.

(56) References Cited

U.S. PATENT DOCUMENTS

| 8,404,264 B2 | 3/2013 | Ameer et al. |
| 8,580,912 B2 | 11/2013 | Ameer et al. |
| 9,257,723 B2 | 2/2016 | Crepel et al. |
| 2003/0194480 A1 | 10/2003 | Leukel et al. |
| 2007/0128152 A1 | 6/2007 | Hadba et al. |
| 2009/0325859 A1 | 12/2009 | Ameer et al. |
| 2010/0036476 A1 | 2/2010 | Ameer et al. |
| 2013/0211500 A1 | 8/2013 | Kibbe et al. |
| 2014/0037588 A1 | 2/2014 | Yang et al. |
| 2014/0147472 A1 | 5/2014 | Elimelech et al. |
| 2015/0315434 A1* | 11/2015 | Steele ............... A61L 24/001 514/772.1 |

FOREIGN PATENT DOCUMENTS

| CN | 1416437 A | 5/2003 |
| CN | 102596275 A | 7/2012 |
| CN | 102917699 A | 2/2013 |
| CN | 106715399 A | 5/2017 |
| EP | 1 719 530 A2 | 11/2006 |
| EP | 3 162 352 A1 | 5/2017 |
| WO | 2014/081391 A1 | 5/2014 |

OTHER PUBLICATIONS

Mahapatra et al. (J. Nanobiotechnology (2011) 9:55).*
Feng et al., "Elastic Light Tunable Tissue Adhesive Dendrimers," *Macromolecular Bioscience* 16(7):1072-1082, 2016.
Bender et al., "Convenient Synthesis of a [1-$^{14}$C]Diazirinylbenzoic Acid as a Photoaffinity Label for Binding Studies of V-ATPase Inhibitors," *Eur. J. Org. Chem.*:3870-3878, 2007.
Bouten et al., "The chemistry of tissue adhesive materials," *Progress in Polymer Science* 39:1375-1405, 2014.
Bruns et al., "Using Tissue Adhesive for Wound Repair: A Practical Guide to Dermabond," *Am Fam Physician* 61(5):1383-1388, 2000. (6 pages).
Djordjevic et al., "Osteoblast Biocompatibility on Poly(octanediol citrate)/ Sebacate Elastomers with Controlled Wettability," *Journal of Biomaterials Science* 21:1039-1050, 2010 (13 pages).
Djordjevic et al., "Polyoctanediol Citrate/Sebacate Bioelastomer Films: Surface Morphology, Chemistry and Functionality," *Journal of Biomaterials Science* 21:237-251, 2010 (16 pages).
Djordjevic et al., "Synthesis and characterization of novel citric acid-based polyester elastomers," *Polymer* 50:1682-1691, 2009. (11 pages).
Feng et al., "Elastic Light Tunable Tissue Adhesive Dendrimers," *Macromol. Biosci.* 16:1072-1082, 2016.
Fukase et al., "4-Nitrobenzyl Group for Protection of Hydorxyl Functions," *Tetrahedron Letters* 31(3):389-392, 1990.
Mogal et al., "Novel On-Demand Bioadhesion to Soft Tissue in Wet Environments," *Macromol. Biosci.* 14:478-484, 2014.
Moradi et al., "Fabrication and characterization of elastomeric scaffolds comprised of a citric acid-based polyester/hydroxyapatite microcomposite," *Materials and Design* 50:446-450, 2013.

(Continued)

*Primary Examiner* — Shirley V Gembeh
(74) *Attorney, Agent, or Firm* — Seed IP Law Group LLP

(57) ABSTRACT

According to the present disclosure, a bioadhesive formulation is provided. The bioadhesive formulation comprises a polycaprolactone dendrimer having a dendrimer core and a plurality of polycaprolactone chains extending from the dendrimer core, wherein at least one of the polycaprolactone chains has an end which is covalently attached with a diazirine, and wherein the diazirine converts to a carbene or a diazoalkyl when a stimulant is applied to the bioadhesive formulation. Methods of forming the bioadhesive formulation are also provided. The bioadhesive could be used in (i) the prevention of thrombosis from tissue fixation and/or (ii) the relief of discomfort and/or pain during and/or after surgery. Preferably, the bioadhesive formulation further comprises a hygroscopic additive, an antithrombotic agent, and/or an anaesthetic agent.

10 Claims, 9 Drawing Sheets

(56) References Cited

OTHER PUBLICATIONS

Ping et al., "Adhesive curing through low-voltage activation," *Nature Communications* 6(8050):1-9, 2015.
Qiu et al., "A citric acid-based hydroxyapatite composite for orthopedic implants," *Biomaterials* 27:5845-5854, 2006.
Serrano et al., "Synthesis of novel lidocaine-releasing poly(diol-co-citrate) elastomers by using deep eutectic solvents," *Chem. Commun.* 48:579-581, 2012.
Shirazi et al., "Processing and characterization of elastomeric polycaprolactone triol-citrate coatings for biomedical applications," *Progress in Organic Coatings* 77:821-829, 2014.
Tran et al., "Citrate-Based Biomaterials and Their Applications in Regenerative Engineering," *Annu. Rev. Mater. Res.* 45:277-310, 2015. (36 pages).
Yang et al., "A Thermoresponsive Biodegradable Polymer with Intrinsic Antioxidant Properties," *Biomacromolecules* 15:3942-3952, 2014.
Yang et al., "Modulating Expanded Polytetrafluoroethylene Vascular Graft Host Response via Citric Acid-Based Biodegradable Elastomers," *Adv. Mater.* 18:1493-1498, 2006.
Yang et al., "Novel Biphasic Elastomeric Scaffold for Small-Diameter Blood Vessel Tissue Engineering," *Tissue Engineering* 11(11/12):1876-1886, 2005.
Yang et al., "Synthesis and evaluation of poly(diol citrate) biodegradable elastomers," *Biomaterials* 27:1889-1898, 2006.

\* cited by examiner

A) Complete anastomosis construct    Upon harvesting after 7 days

B) HM, Aorta

C) FM, Illiac

HYGROSCOPIC, CROSSLINKING COATINGS AND BIOADHESIVES

CROSS-REFERENCE TO RELATED APPLICATION

This application claims the benefit of priority of Singapore Patent Application No. 10201707244R, filed 6 Sep. 2017, the content of it being hereby incorporated by reference in its entirety for all purposes.

TECHNICAL FIELD

The present disclosure relates to a bioadhesive formulation and its uses. The present disclosure also relates to methods of forming such a bioadhesive formulation.

BACKGROUND

Conventional methods of tissue fixation in clinical practice involve mechanical technologies such as sutures, pins, wires and screws. Such mechanical tissue closures tend to inflict damage on the tissue, require longer duration of application and/or elicit an immunological response.

An alternative may be the application of glue-like materials, referred to as "bioadhesives" in this disclosure, which have been developed to replace the mechanical technologies described above. Several bioadhesive products are commercially available, and they may be derived from synthetic polymers (e.g. cyanoacrylates, polyesters, dendrimers, polyurethanes), proteins (e.g. fibrin, gelatin, albumin), polysaccharides (e.g. chitosan, dextran, chondroitin sulfate, hyaluronic acid), and gecko-inspired or mussel adhesive proteins. For example, bioadhesives used in clinical practice typically include cyanoacrylate based adhesives (e.g. Dermabond) and protein based sealants (e.g. Tisseel, TachoComb, TachoSil).

Dermabond is a commercial tissue adhesive designed to replace sutures for incisional or laceration repair, which when applied, forms a strong bond across wound edges, and this type of adhesive promotes healing below the skin barrier. This adhesive provides a flexible water-resistant wound coating with cosmetic outcomes that are comparable to traditional wound sealing methods. Cyanoacrylate tissue adhesives, such as Dermabond, function through moisture-induced polymerization on the skin surface, and the formed polymer adhesive binds to the top epithelial layer and seals two wound edges via a cyanoacrylate bridge. This, however, is an exothermic reaction that generates heat and possibly formaldehyde, which may cause inflammation at the site of application, posing a considerable drawback for the use of cyanoacrylate bioadhesives in minimally invasive surgery procedures. Moreover, when cyanoacrylate degrades, the toxicity of its leachants has to be considered. The application of cyanoacrylate adhesives, such as Dermabond, is therefore not suitable for severely contaminated wounds, ulcers, punctured wounds, mucous membranes (including mucocutaneous junctions) or areas having high moisture content.

Another alternative or adjunct to sutures and staples, protein based sealants, such as Tisseel and other fibrin bioadhesives, have been used. Such sealants contain fibrinogen and thrombin, which are used in combination as a hemostatic agent for cardiovascular surgery. Protein based sealants, e.g. fibrin based bioadhesives, result in minimal inflammation, and may be considered biocompatible and biodegradable for an application duration ranging from days to weeks. This type of sealants is typically applied using a dual syringe system that separately contains thrombin and fibrin. The drawbacks of such sealants include (i) complicated preparation/application procedures, (ii) derivation from human plasma which poses a risk of virus contamination, (iii) derivation from bovine plasma and immunological, allergenic or anaphalytic reaction may be triggered, (iv) poor adhesion compared to synthetic glues, and (v) a dry surface to work.

Apart from the above, bioadhesives based on free radical and carbene precursors that can be covalently attached to either solid substrates or dendrimer systems have been explored. One of such bioadhesives is a water soluble, injectable bioadhesive (PAMAM-grafted-diazirine) based on polyamidoamine (PAMAM) dendrimers grafted with 4-[3-(trifluoromethyl)-3H-diazirin-3-yl] benzyl bromide.

When such a bioadhesive is exposed to ultraviolet (UV) light or low-voltage activation, the conjugated diazirines form covalent crosslinkages with hydrated tissues. Such PAMAM dendrimer bioadhesives, however, have their limitations. For instance, they do not dispense properly as neat (i.e. undiluted) formulations because the resulting viscosity of such formulations are typically too high (more than 100 Pa·s). Consequently, such bioadhesives do not dispense well through syringes. If PAMAM dendrimer bioadhesives are diluted in aqueous solvents (e.g. saline) to decrease their viscosity for syringe application, the dilution may compromise long-term storage (e.g. 12 months or more), even at room temperatures, due to hydrolysis of the carbene precursor (e.g. diazirine), and the dilution does not allow for further absorption or dispersion of water on wet substrates, which may prevent homogenous adhesion and/or crosslinking.

Moreover, diluting the PAMAM dendrimer bioadhesives in an aqueous solvent, or even an organic solvent (e g ethanol), may limit the amount of internal crosslinking between polymers and/or prevent homogenous adhesion to a tissue, as the aqueous or solvent molecules compete for intramolecular crosslinking to the dendrimer, thus affecting material properties and preventing formation of tough and elastic polymer networks. Adversely, the crosslinked PAMAM dendrimer bioadhesives result in brittle hydrogels having strong surface adhesion but weak matrix properties.

Another limitation of PAMAM dendrimer bioadhesives is their high production cost (more than USD 10,000 per kg), and this makes it undesirable to scale up their production.

In light of the above, there is a need to provide for a bioadhesive that ameliorates one or more of the abovementioned limitations. The bioadhesive should at least be capable of sealing tissue wound.

SUMMARY

In a first aspect, there is provided for a bioadhesive formulation comprising a polycaprolactone dendrimer having a dendrimer core and a plurality of polycaprolactone chains extending from the dendrimer core, wherein at least one of the polycaprolactone chains has an end which is covalently attached with a diazirine, and wherein the diazirine converts to a carbene and/or a diazoalkyl when a stimulant is applied to the bioadhesive formulation.

In another aspect, there is provided for a bioadhesive formulation described according to the first aspect for use in therapy.

In another aspect, there is provided for a bioadhesive formulation described according to the first aspect for use in (i) the prevention of thrombosis from tissue fixation and/or (ii) the relief of discomfort and/or pain during and/or after surgery.

In another aspect, there is provided for use of a bioadhesive formulation described according to the first aspect in the manufacture of a porous bioadhesive composite for (i) the prevention of thrombosis from tissue fixation and/or (ii) the relief of discomfort and/or pain during and/or after surgery.

In another aspect, there is provided for a method of preventing thrombosis from tissue fixation, comprising:

implanting a bioadhesive formulation to a target site, wherein the bioadhesive formulation comprises an antithrombotic agent and a polycaprolactone dendrimer, wherein the polycaprolactone dendrimer has a dendrimer core and a plurality of polycaprolactone chains extending from the dendrimer core, wherein at least one of the polycaprolactone chains has an end which is covalently attached with a diazirine; and applying a stimulant to the bioadhesive formulation to convert the diazirine to a carbene and/or a diazoalkyl, thereby curing the bioadhesive formulation to form a porous bioadhesive composite having one or more surfaces incorporated with the antithrombotic agent.

In another aspect, there is provided for a method of relieving discomfort and/or pain during and/or after surgery, comprising:

implanting a bioadhesive formulation to a target site, wherein the bioadhesive formulation comprises an anaesthetic agent and a polycaprolactone dendrimer, wherein the polycaprolactone dendrimer has a dendrimer core and a plurality of polycaprolactone chains extending from the dendrimer core, wherein at least one of the polycaprolactone chains has an end which is covalently attached with a diazirine; and applying a stimulant to the bioadhesive formulation to convert the diazirine to a carbene and/or a diazoalkyl, thereby curing the bioadhesive formulation to form a porous bioadhesive composite incorporated with the anaesthetic agent, wherein the anaesthetic agent is released from the porous bioadhesive composite when the porous bioadhesive composite is subjected to stress.

In another aspect, there is provided for a method of tissue fixation, comprising:

implanting a bioadhesive formulation to a tissue to be fixed, wherein the bioadhesive formulation comprises a polycaprolactone dendrimer having a dendrimer core and a plurality of polycaprolactone chains extending from the dendrimer core, wherein at least one of the polycaprolactone chains has an end which is covalently attached with a diazirine; and applying a stimulant to the bioadhesive formulation to convert the diazirine to a carbene and/or a diazoalkyl, thereby curing the bioadhesive formulation for tissue fixation.

In another aspect, there is provided for a method of forming a bioadhesive formulation, comprising:

mixing a polycaprolactone dendrimer precursor comprising one or more —OH and/or —COOH groups with a diazirine precursor in the presence of a mild base to form a mixture comprising a polycaprolactone dendrimer, wherein the diazirine precursor is represented by the formula:

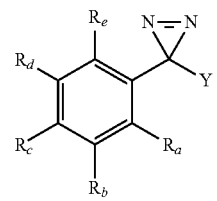

wherein at least one of $R_a$ to $R_e$ is hydrogen or —$C_{1-12}$ alkyl substituted with one or more halogens;

wherein Y is hydrogen, halogen or —$C_{1-12}$ alkyl substituted with one or more halogens;

filtering the mixture with a molecular sieve; and adding water to the filtered mixture to precipitate the polycaprolactone dendrimer, wherein the polycaprolactone dendrimer comprises a dendrimer core and a plurality of polycaprolactone chains extending from the dendrimer core, wherein at least one of the polycaprolactone chains has an end which is covalently attached with a diazirine via an ether linkage or an ester linkage, and wherein the diazirine converts to a carbene and/or a diazoalkyl when a stimulant is applied to the bioadhesive formulation.

In another aspect, there is provided for a method of forming a bioadhesive formulation, comprising:

mixing a polycaprolactone dendrimer precursor comprising one or more —OH and/or —COOH groups with a diazirine precursor in the presence of a mild base to form a suspension comprising a polycaprolactone dendrimer, wherein the diazirine precursor is represented by the formula:

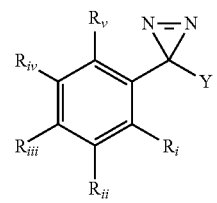

wherein at least one of $R_i$ to $R_v$ is hydrogen or —$R_{vi}C(=O)$—Z;

wherein $R_{vi}$ is a bond or —$C_{1-12}$ alkyl- which is unsubstituted or substituted with one or more halogens;

wherein Z is a halogen;

wherein Y is hydrogen, halogen or —$C_{1-12}$ alkyl substituted with one or more halogens; and extracting the polycaprolactone dendrimer from the suspension, wherein the polycaprolactone dendrimer comprises a dendrimer core and a plurality of polycaprolactone chains extending from the dendrimer core, wherein at least one of the polycaprolactone chains has an end which is covalently attached with a diazirine via an ester linkage or an anhydride linkage, and wherein the diazirine converts to a carbene and/or a diazoalkyl when a stimulant is applied to the bioadhesive formulation.

BRIEF DESCRIPTION OF THE DRAWINGS

The drawings are not necessarily to scale, emphasis instead generally being placed upon illustrating the principles of the invention. In the following description, various embodiments of the present disclosure are described with reference to the following drawings, in which:

FIG. 1B shows the rheometry results for G' of PCLT-D70/CA bioadhesives having different concentrations of CA compared to pure PCLT-D used as control, upon UV activation at 120 mW·cm$^{-2}$.

FIG. 2A specifically shows the exposed rat liver.

FIG. 2B specifically shows the application of a thin layer of the raw PCLT-D70/CA composite.

FIG. 2C specifically shows the marked area (dashed line) that is applied with the PCLT-D70/CA composite.

FIG. 2D is used to specifically demonstrate UVA activated crosslinking at 70 mW·cm$^{-2}$ for 2 mins.

FIG. 2E specifically shows the crosslinked composite after 2 mins of exposure to UVA light.

FIG. 2F specifically shows the solidified foam composite and tissue interface strained manually with tweezers.

FIG. 4A specifically shows the shear adhesion of pure polymer dendrimer PCLT-D70 at 350 mW·cm$^{-2}$ UVA intensity that was used as control.

FIG. 4B specifically shows the PCLT-D70/HA (50%) adhesion strength at 350 mW·cm$^{-2}$ UVA intensity.

FIG. 7A specifically shows a scanning electron microscopy (SEM) image recorded for a PLGA control. Thin-width arrows refer to platelets in inactivated/resting stage while thick-width arrows refer to activated platelets. The scale bar represents 10 μm.

FIG. 7B specifically shows a SEM image recorded for PCLT-D. Thin-width arrows refer to platelets in inactivated or resting stage while thick-width arrows refer to activated platelets. The scale bar represents 10 μm.

FIG. 7C specifically shows a SEM image recorded for PCLT-D with sebacic acid (30%). Thin-width arrows refer to platelets in inactivated or resting stage while thick-width arrows refer to activated platelets. The scale bar represents 10 μm.

DETAILED DESCRIPTION

Figure 1:
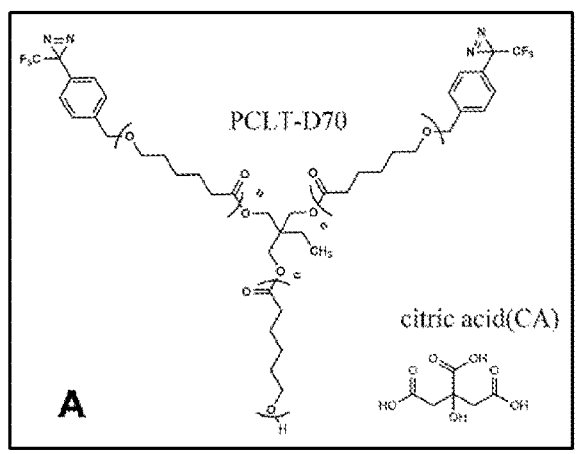
FIG. 1A shows the chemical structures of a polycaprolactone dendrimer grafted with 70% of diazirine (PCLT-D70), and the citric acid (CA) additive, for a bioadhesive composition.
FIG. 1B shows a plot of storage modulus, G', against time. Specifically.
FIG. 1C shows the formation of diazoalkyl functional groups and the depletion of diazirine functional groups from PCLT-D70 at 10 seconds after exposure to a low intensity ultraviolet A (UVA) irradiation (1 J·cm$^{-2}$ at 365 nm) via a FTIR (Fourier-Transform Infrared) spectrum.
Figure 1:
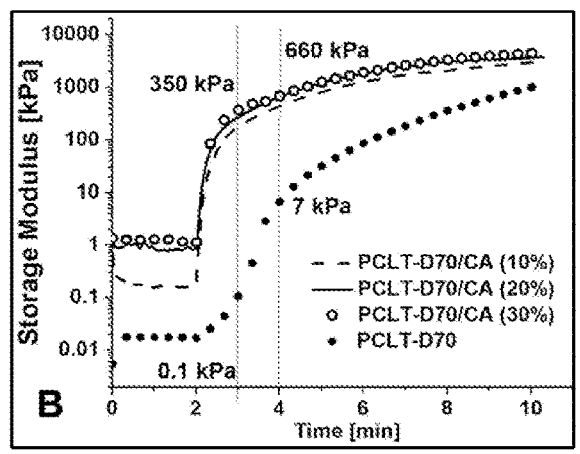
Figure 1:
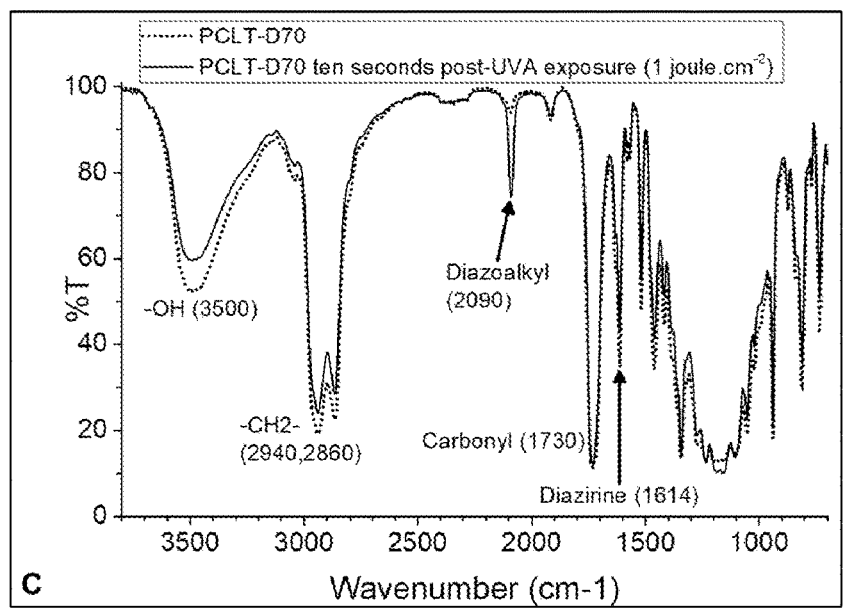

The following detailed description refers to the accompanying drawings that show, by way of illustration, specific details and embodiments in which the invention may be practiced.

The various embodiments are described in sufficient detail to enable those skilled in the art to practice the invention. Other embodiments may be utilized, and changes may be made without departing from the scope of the invention. The various embodiments are not necessarily mutually exclusive, as some embodiments can be combined with one or more other embodiments to form new embodiments.

Features that are described in the context of an embodiment may correspondingly be applicable to the same or similar features in the other embodiments. Features that are described in the context of an embodiment may correspondingly be applicable to the other embodiments, even if not explicitly described in these other embodiments. Furthermore, additions and/or combinations and/or alternatives as described for a feature in the context of an embodiment may correspondingly be applicable to the same or similar feature in the other embodiments.

Various embodiments of the present disclosure refer to a bioadhesive formulation of the first aspect as described above and uses of such a bioadhesive formulation. The various embodiments also refer to the methods of forming such a bioadhesive formulation.

The bioadhesive formulation is advantageous in that it circumvents the damage resulting from suturing or stapling a tissue opening (e.g. wound), as it is simply applied to the tissue opening and a stimulant can be used to cure the bioadhesive formulation to form a bioadhesive composite that seals or fixes the tissue opening. In the context of the present disclosure, fixing of a tissue opening means that the tissues are maintained in a position that keeps the tissue opening sealed.

When the present bioadhesive formulation is cured, no exothermic reaction occurs and no toxic materials are formed or leached out. The present bioadhesive formulation, when cured, becomes a bioresorbable (i.e. biodegradable and/or can be dissolved or absorbed by a human body) bioadhesive composite (e.g. a solid sealant). Hence, the present bioadhesive formulation is advantageous over conventional cyanoacrylate bioadhesives that face such issues.

The present bioadhesive formulation is advantageous over protein (e.g. thrombin and fibrin) based sealants, as such protein based sealants may be derived from human plasma and thus pose a risk of virus contamination or cause adverse immunological, allergenic or anaphalytic reactions when applied to another subject (e.g. human). Such protein based sealants may require the surface to be dried for application. The present bioadhesive formulation, however, is not constrained by such issues, as it is neither derived from human plasma nor require a dry surface for working on.

The present bioadhesive formulation is superior over conventional bioadhesives derived from polyamidoamine (PAMAM) dendrimers grafted with diazirine (PAMAM-D). This is because such PAMAM bioadhesives cannot be dispensed as a formulation (e.g. via a syringe) in the absence of excess water or an aqueous solvent, as the viscosity of PAMAM-D bioadhesives are too high (more than 100 Pa·s). Even if PAMAM-D bioadhesives are diluted with water or an aqueous solvent, their storage duration (at room temperature) becomes compromised, for example, to less than 12 months, and they tend to form brittle hydrogels with weak matrix properties due to lesser crosslinking when diluted in an aqueous medium. In contrast, the present bioadhesive formulation does not face such issues. Advantageously, the present bioadhesives can be applied (e.g. via a syringe without dilution) to a tissue surface as a liquid formulation.

Advantageously, the present bioadhesive formulation is usable for various applications, which include, without being limited to, prevention of thrombosis when used in combination with an antithrombotic agent, relief of discomfort and/or pain when used in combination with an anaesthetic agent, tissue fixation, therapy, etc. The present bioadhesive formulation can also be used in dental applications, as the present bioadhesive formulation, when cured, have properties comparable to those of bone tissues. The present bioadhesive formulation can further be used in the manufacture of a bioadhesive composite for the various applications or purposes as described herein.

Before going into the details of the present bioadhesive formulation, its uses and the methods of making the present bioadhesive formulation, the definition of certain terms, expressions and phrases are provided as follows.

The phrase "organic solvent" as used herein refers to a carbon-based liquid that is capable of dissolving an organic compound. The organic solvent may be polar or non-polar.

The term "covalent" as used herein means that two atoms are bonded together through the sharing of electrons.

The phrase "ether linkage" as used herein means that two chemical moieties are connected to each other via a —O— group.

The phrase "ester linkage" as used herein means that two chemical moieties are connected to each other via a —COO— group.

The phrase "anhydride linkage" as used herein means that two chemical moieties are connected to each other via a —C(=O)OC(=O)— group.

In the context of the present disclosure, the term "hydrophobic" refers to substances that are insoluble or substantially insoluble in water, saline solution, or phosphate buffered saline solution, but are soluble in one or more organic solvents.

The term "alkyl" as a group or part of a group refers to a straight or branched saturated aliphatic group having from 1 to 12 carbon atoms, preferably having 1 to 10 carbon atoms or 1 to 6 carbon atoms unless otherwise noted. For example, a "$C_{1-12}$ alkyl" group can have 1, 2, 3, 4, 5, 6, 7, 8, 9, 10, 11 or 12 carbon atoms. The term "alkyl" includes, but is not limited to, methyl, ethyl, 1-propyl, isopropyl, 1-butyl, 2-butyl, isobutyl, tert-butyl, amyl, 1,2-dimethylpropyl, 1,1-dimethylpropyl, pentyl, isopentyl, hexyl, 4-methylpentyl, 1-methylpentyl, 2-methylpentyl, 3-methylpentyl, 2,2-dimethylbutyl, 3,3-dimethylbutyl, 1,2-dimethylbutyl, 1,3-dimethylbutyl, 1,2,2-trimethylpropyl, 1,1,2-trimethylpropyl, 2-ethylpentyl, 3-ethylpentyl, heptyl, 1-methylhexyl, 2,2-dimethylpentyl, 3,3-dimethylpentyl, 4,4-dimethylpentyl, 1,2-dimethylpentyl, 1,3-dimethylpentyl, 1,4-dimethylpentyl, 1,2,3-trimethylbutyl, 1,1,2-trimethylbutyl, 1,1,3-trimethylbutyl, 5-methylheptyl, 1-methylheptyl, octyl, nonyl, decyl, and the like.

The term "halogen" or "halide" refers to an element from group 17 of the periodic table, and includes, for example, fluorine, chlorine, bromine, etc.

The terms "bioadhesive" and "sealant" are used interchangeably in the present disclosure.

The word "substantially" does not exclude "completely" e.g. a composition which is "substantially free" from Y may be completely free from Y. Where necessary, the word "substantially" may be omitted from the definition of the invention.

In the context of various embodiments, the articles "a", "an" and "the" as used with regard to a feature or element include a reference to one or more of the features or elements.

In the context of various embodiments, the term "about" or "approximately" as applied to a numeric value encompasses the exact value and a reasonable variance.

As used herein, the term "and/or" includes any and all combinations of one or more of the associated listed items.

Unless specified otherwise, the terms "comprising" and "comprise", and grammatical variants thereof, are intended to represent "open" or "inclusive" language such that they include recited elements but also permit inclusion of additional, unrecited elements.

Various embodiments and details of the present bioadhesive formulation, its uses and methods of forming the present bioadhesive formulation, are described as follows.

In the present disclosure, there is provided for a bioadhesive formulation comprising a polycaprolactone dendrimer having a dendrimer core and a plurality of polycaprolactone chains extending from the dendrimer core, wherein at least one of the polycaprolactone chains has an end which is covalently attached with a diazirine, and wherein the diazirine converts to a carbene and/or a diazoalkyl when a stimulant is applied to the bioadhesive formulation.

Polycaprolactone is a bioresorbable polymer, and hence, can be advantageously exploited for production of medical devices, drug delivery systems, etc. The present bioadhesive formulation is based on polycaprolactone, and the polycaprolactone is in the form of a polycaprolactone dendrimer. The polycaprolactone dendrimer may be derived from a polycaprolactone dendrimer precursor that has a number average molar mass that is less than 2000 Da, which allows easy manipulation of rheological and viscoelastic properties. The polycaprolactone dendrimer precursor may come in a range of molecular weights and star-shaped geometries that provide for multiple functional groups to be grafted on. For example, the polycaprolactone dendrimer precursor may be a polycaprolactone dendrimer having one or more —OH and/or —COOH groups. The polycaprolactone dendrimer precursor may be a polycaprolactone polyol dendrimer and non-limiting examples include polycaprolactone diol dendrimer, polycaprolactone triol dendrimer, polycaprolactone tetrol dendrimer, polycaprolactone hexol dendrimer, etc.

The polycaprolactone dendrimer precursor may be synthesized from a polycaprolactone initiator. The polycaprolactone initiator may form the polycaprolactone dendrimer core. The polycaprolactone initiator may be a non-toxic precursor such as citric acid. Using the polycaprolactone triol dendrimer precursor as an example, it may be synthesized from citric acid. Citric acid may be present during human metabolism and is therefore considered a non-toxic, biodegradable and biocompatible initiator. This property of having polycaprolactone chains grafted onto citric acid (to form the triol) is advantageous, as citric acid can react with both linear and branched polyalcohols to yield polyester elastomers with a range of mechanical properties that allow for processing through melting or thermo-polymerization techniques into various shapes and forms, such as biodegradable coatings, porous tissue engineering scaffolds, bone fixation devices, drug delivery systems, thermoresponsive injectable hydrogels, etc. Accordingly, the present bioadhesive formulation, which is based on the polycaprolactone dendrimer, possesses such an advantage.

When a diazirine precursor and the polycaprolactone dendrimer precursor react to form the present bioadhesive formulation comprised of a polycaprolactone grafted diazirine dendrimer (PCLT-D), the issues encountered with PAMAM dendrimers, including those of PAMAM-D dendrimers, can be overcome. For instance, bioadhesives of PAMAM dendrimers have viscosities of 100 Pa·s at room temperature but the present bioadhesive has a viscosity of about 1 Pa·s and the lower viscosity allows for convenient syringe application without dilution. Moreover, the storage duration of the present bioadhesive formulation is not compromised to less than 12 months, even with dilution. Crosslinking of the present polycaprolactone dendrimer during curing is also not compromised since dilution in aqueous medium, or even an organic solvent, can be avoided.

The term "dendrimer" as used herein is to be distinguished from a linear polymer having various chemical moieties branching from one or more positions along its linear straight-chain backbone. Such a linear polymer may be called a strand of polymer due to its linear structure. A dendrimer, in contrast, is not such a linear polymer. Instead, a dendrimer has a plurality of chemical moieties or molecules extending to or from a single central core (i.e. the dendrimer core). The plurality of chemical moieties or molecules may be same or different. In the context of the present disclosure, the plurality of chemical moieties or molecules are the polycaprolactone chains. Each of the polycaprolactone chains in the polycaprolactone dendrimer precursor may have at least one —OH and/or at least one —COOH group. The —COOH group may be present when the —OH group is oxidized. As for the polycaprolactone dendrimer, at least one of the polycaprolactone chains has at least one diazirine covalently attached to one end of the polycaprolactone chain. This end may be the end of the polycaprolactone chain that extends away from the dendrimer core. This end may be a terminal end of the polycaprolactone chain that extends away from the dendrimer core. The expression "terminal", when used with respect to the polycaprolactone chain, refers to the nearest or furthest atom in that chain relative to the dendrimer core. For example, the diazirine may be covalently attached to the terminal carbon of a polycaprolactone chain that is positioned furthest away from the dendrimer core. The term "conjugated" and "grafted" may be used interchangeably with the term "attached".

Meanwhile, the other end of the polycaprolactone chain that is not attached with the diazirine, the —OH group, and/or the —COOH group, is connected to the dendrimer core or may be considered as part of the dendrimer core. The dendrimer core, in a non-limiting example already described above, may be formed from the citric acid initiator.

In various embodiments, each of the polycaprolactone chains may comprise one or more repeating units of:

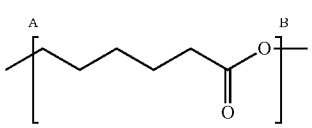

wherein part A of each repeating unit extends away from the dendrimer core and part B of each repeating unit extends toward the dendrimer core. In various embodiments, part A of the repeating unit arranged furthest away from the dendrimer core forms the end at which the diazirine is covalently attached to the polycaprolactone chain for at least one of the polycaprolactone chains. Accordingly, in various embodiments, each of the polycaprolactone chains may comprise one or more repeating units of:

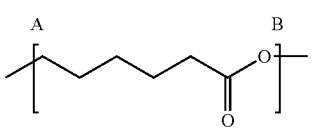

wherein part A of each repeating unit extends away from the dendrimer core and part B of each repeating unit extends toward the dendrimer core, and wherein in the at least one polycaprolactone chain having an end which is covalently attached with the diazirine, part A of the repeating unit arranged furthest away from the dendrimer core forms the end at which the diazirine is covalently attached to the at least one polycaprolactone chain. In embodiments where there is only one of such repeating unit, that one repeating unit may be considered as the repeating unit that is arranged furthest away from the dendrimer core. In such embodiments, part A of that one repeating unit forms the end at which there is a terminal atom that is covalently attached with or to a diazirine. The phrase "repeating unit" is a part of a polymer whose repetition would produce a complete polymer chain.

In various embodiments, part A of the repeating unit arranged furthest away from the dendrimer core forms the end at which there is an oxygen for forming an ether linkage, an ester linkage, or an anhydride linkage, with the diazirine. In various embodiments, the terminal atom at, or connected to, part A of the repeating unit that is arranged furthest away from the dendrimer core may be an oxygen. The oxygen exists, for forming an ether linkage, an ester linkage, or an anhydride linkage, as the terminal end (part A) of the one or more repeating units forming the polycaprolactone chain may be a —OH and/or —COOH group. In some examples, in cases where that end (part A) of the one or more repeating units are of a —OH group or a —COOH group, whether an ether linkage, an ester linkage, or an anhydride linkage, is formed depends on the functional group (e.g. a halide, or an acyl halide represented by —C(=O)W, wherein W represents a halogen) of the diazrine precursor that reacts with that end (part A) of the polycaprolactone chain when forming the polycaprolactone dendrimer.

In various embodiments, the diazrine that is covalently attached to the polycaprolactone chain or that end (part A) of the polycaprolactone chain may be a diazirine represented by the formula:

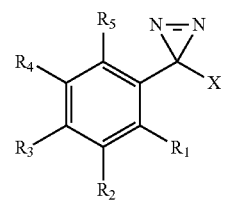

wherein at least one of $R_1$ to $R_5$ is hydrogen, —$C_{1-12}$ alkyl- which is unsubstituted or substituted with one or more halogens, or —$R_6C(=O)$—, wherein the —$C_{1-12}$ alkyl- in at least one of $R_1$ to $R_5$ is covalently attached to the oxygen to form an ether linkage or an ester linkage with the polycaprolactone chain, wherein the —$R_6C(=O)$— in at least one of $R_1$ to $R_5$ is covalently attached to the oxygen to form an ester linkage or an anhydride linkage with the polycaprolactone chain, wherein $R_6$ is a bond or —$C_{1-12}$ alkyl- which is unsubstituted or substituted with one or more halogens, and wherein X is hydrogen, halogen or —$C_{1-12}$ alkyl substituted with one or more halogens. The halogen may be fluorine, chlorine, bromine, etc. As a non-limiting example, $R_3$ may be a —$C_{1-12}$ alkyl- substituted with a terminal halogen while $R_1$, $R_2$, $R_4$ and $R_5$ may be hydrogen and X may be —$C_{1-12}$ alkyl substituted with more than one halogen. When X is chlorine, more carbene may be converted from the diazirine. For example, 99% or more of the diazirine may be converted to carbene, which means that 1% or less of the diazirine may be converted to diazoalkyl. This may be used to influence the ratio of diazoalkyl/carbene formation.

In certain embodiments, the diazirine that is covalently attached may be a diazirine comprising:

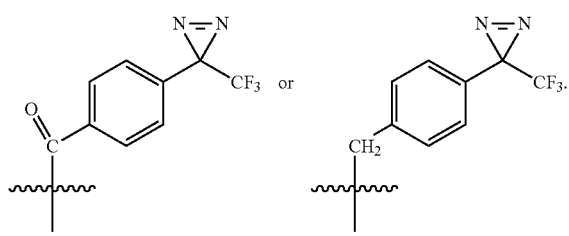 [SMILES: *C(=O)c1ccc(C2(C(F)(F)F)N=N2)cc1 ; *Cc1ccc(C2(C(F)(F)F)N=N2)cc1]

These diazirines are advantageous in that they can be grafted onto the polycaprolactone dendrimers via a one-step grafting process. That is to say, as an example, the reaction mechanism by which the diazrine covalently attaches to the polycaprolactone dendrimer via an ether linkage may be straightforward. When an ester linkage is formed for the covalent attachment of these diazirines, a higher yield may be obtained. The crosslinking reaction may be kinetically faster, as the reaction may be more sensitive to light for activation.

The covalent attachment of a diazirine to the polycaprolactone chain is advantageous for the bioadhesive formulation as the diazirine is convertible to a carbene or a diazoalkyl, depending on the stimulant applied. In other words, each of the polycaprolactone chains that is covalently attached with a diazirine may become a polycaprolactone chain that is covalently attached with either a carbene or a diazoalkyl, depending on the stimulant that is applied.

The term "carbene" as used herein refers to a carbon having two valence electrons, as represented by —C:—, wherein the ":" refers to the two valence electrons. When the diazirine is converted into a carbene, random non-specific crosslinking can occur, as carbene can form crosslinkages with any nearby molecules containing a Q-H bond, where Q may be C, N, O or S. Such non-specific crosslinking imparts versatility to the bioadhesive as it can then crosslink to any tissue surface to improve adhesion, and/or form internal crosslinkages with any other molecules or chemical moieties in the bioadhesive formulation to strengthen the matrix of the bioadhesive formulation when it is cured. For example, the carbene can form crosslinkages with any other nearby polycaprolactone chain of the polycaprolactone dendrimer. As forming of the crosslinkages is random and non-specific, more internal crosslinkages can be formed to result in a bioadhesive that is not brittle.

Meanwhile, crosslinkages resulting from the diazoalkyl are specific in that it specifically crosslinks with nucleophilic functional groups, such as —COOH groups, —OH groups, —SH groups, etc. This is advantageous if specific crosslinkages are required. The term "diazoalkyl" as used herein may be represented by:

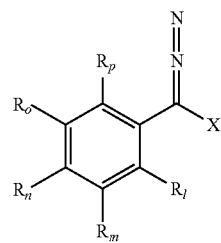

wherein at least one of $R_1$ to $R_p$ is hydrogen, —$C_{1-12}$ alkyl- which is unsubstituted or substituted with one or more halogens, or —$R_qC(=O)$—. The —$C_{1-12}$ alkyl- in at least one of $R_1$ to $R_p$ may be covalently attached to an oxygen that forms an ether linkage or an ester linkage with the polycaprolactone chain. The —$R_qC(=O)$— in at least one of $R_1$ to $R_p$ may be covalently attached to an oxygen that forms an ester linkage or an anhydride linkage with the polycaprolactone chain. $R_q$ is a bond or —$C_{1-12}$ alkyl- which is unsubstituted or substituted with one or more halogens. X is hydrogen, halogen or —$C_{1-12}$ alkyl substituted with one or more halogens. The halogen may be fluorine, chlorine, bromine, etc. When X contains a halogen, the reaction of any C—H bonds with the "N=N=" group may be prevented. When X is chlorine, less diazoalkyl may be converted from the diazirine as mentioned above. By controlling the ratio of diazoalkyl/carbene formed, the type of crosslinking may be controlled as well. The diazoalkyl of the present disclosure, as represented by the formula shown above, is converted from the diazirine that is covalently attached to the polycaprolactone chain, wherein such a diazirine is already described above.

The conversion of diazirine into carbene or diazoalkyl, by a stimulant, can be used to alter the amount of crosslinkages internally formed within the bioadhesive. Said differently, the diazirine advantageously allows for different degrees of curing, depending on the stimulant used. The degree of curing may be used to adjust the porosity of the resultant cured bioadhesive. The term "curing" as used herein refers to the hardening or toughening of a substance through formation of covalent crosslinkages.

The stimulant that is applied may be or may include electromagnetic irradiation having one or more wavelengths from 315 nm to 1400 nm, 315 nm to 400 nm, 680 nm to 730 nm, 650 nm to 750 nm, 365 nm, etc. The stimulant that is applied may also be or may also include electromagnetic irradiation having one or more intensities in the range of 1 mW·cm$^{-2}$ to 1000 mW·cm$^{-2}$. For example, ultraviolet A (UVA) having a high intensity and a low intensity that converts diazirine to carbene and diazoalkyl, respectively, may be irradiated onto the bioadhesive formulation that is applied onto a tissue opening. The expression "ultraviolet A" refers to electromagnetic radiation having wavelengths in the range of 315 nm to 400 nm. In another example, near-infrared rays of a single intensity may be irradiated onto the bioadhesive formulation to convert diazirine into either carbene or diazoalkyl. Depending on the stimulant used, the polycaprolactone dendrimer may be cured from some polycaprolactone chains having carbene and some polycaprolactone chains having diazoalkyl. This means that specific and random non-specific crosslinkages may be formed, depending on the stimulant used.

The stimulant that is applied may also be or may also include a current in the range of 1 mA to 100 mA, 10 mA to 100 mA, 20 mA to 100 mA, 30 mA to 100 mA, 40 mA to 100 mA, 50 mA to 100 mA, 60 mA to 100 mA, 70 mA to 100 mA, 80 mA to 100 mA, 90 mA to 100 mA, 10 mA to 90 mA, 20 mA to 90 mA, 30 mA to 90 mA, 40 mA to 90 mA, 50 mA to 90 mA, 60 mA to 90 mA, 70 mA to 90 mA, 80 mA to 90 mA, 10 mA to 80 mA, 20 mA to 80 mA, 30 mA to 80 mA, 40 mA to 80 mA, 50 mA to 80 mA, 60 mA to 80 mA, 70 mA to 80 mA, 10 mA to 70 mA, 20 mA to 70 mA, 30 mA to 70 mA, 40 mA to 70 mA, 50 mA to 70 mA, 60 mA to 70 mA, 10 mA to 60 mA, 20 mA to 60 mA, 30 mA to 60 mA, 40 mA to 60 mA, 50 mA to 60 mA, 10 mA to 50 mA, 20 mA to 50 mA, 30 mA to 50 mA, 40 mA to 50 mA, 10 mA to 40 mA, 20 mA to 40 mA, 30 mA to 40 mA, 10 mA to 30 mA, 20 mA to 30 mA, 10 mA to 20 mA, etc.

The stimulant that is applied may also be or may also include a voltage in the range of +50 V, ±40 V, +30 V, +20 V, +10 V, ±5 V, +2 V, −5 V to 50 V, 2 V to 50 V, etc.

In various embodiments, the stimulant that is applied may comprise (i) electromagnetic radiation having one or more wavelengths from 315 nm to 1400 nm, (ii) electromagnetic radiation having one or more intensities in the range of 1 mW·cm$^{-2}$ to 1000 mW·cm$^{-2}$, (iii) a current in the range of 1 mA to 100 mA and/or (iv) a voltage in the range of ±50 V.

The application of a stimulant to cure the bioadhesive formulation is needed, for example, when the bioadhesive formulation that is applied to a tissue surface is in the form of a liquid formulation. Applying a bioadhesive formulation that is in the form of a liquid is advantageous as it allows for spreading of the bioadhesive formulation to adequately cover the required tissue area. Accordingly, when the liquid formulation is cured due to crosslinkages resulting from the converted carbene and/or diazoalkyl, the bioadhesive formulation becomes a cured bioadhesive. The cured bioadhesive is a hardened bioadhesive that seals or fixes a tissue opening or tissue wound for closure. In various embodiments, the bioadhesive formulation may be in the form of a liquid formulation, wherein the liquid formulation becomes a cured bioadhesive when the stimulant is applied to the bioadhesive formulation.

In certain embodiments, the bioadhesive formulation may comprise or may be use in combination with a hygroscopic additive. The term "hygroscopic" as used herein refers to a substance that absorbs moisture from its surrounding, including the surrounding air. The presence of a hygroscopic additive adds to the advantage of the present bioadhesive formulation. The present bioadhesive formulation is hydrophobic in nature, which allows for adhesion to a tissue having a surface or at least part of a surface that is hydrophobic. With the hygroscopic additive, adhesion to a tissue having a surface or at least part of a surface that is hydrophilic, is improved, and the bioadhesive formulation has improved adhesion to a tissue having both hydrophobic and hydrophilic surfaces. Advantageously, the hygroscopic additive also helps to reduce bioadhesive fouling on hydrophilic surfaces and provides for surface water-hydration. The latter is useful as highly crosslinked non-aqueous liquid bioadhesives tend to have difficulty being applied onto hydrated surfaces or are incompatible with such hydrated surfaces due to their opposing non-aqueous (e.g. hydrophobic) nature. With the hygroscopic additive, the present bioadhesive formulation, when cured, provides for a water-impenetrable sealant and/or coating on the tissue surface that it is applied to, due to its hydrophobic nature, without compromising the improved adhesion with a tissue that has hydrophilic surface. The present bioadhesive formulation, with the hygroscopic additive, is applicable onto both hydrophobic and/or hydrophilic surfaces, rendering the present bioadhesive formulation extremely versatile. An example of the hygroscopic additive may be or may comprise anhydrous citric acid, anhydrous ethanol, anhydrous magnesium sulfate, and/or hydroxyapatite. Other anhydrous biocompatible solvents that form water azeotropes may be suitably used. Other anhydrous biocompatible salts or dessicants may also be suitably used. The limitations of PAMAM dendrimers, as described above, are overcome by the addition of hygroscopic additive(s).

The present bioadhesive formulation may also comprise an antithrombotic agent. This helps to reduce and/or eliminate thrombosis at tissue surface that are applied with the present bioadhesive formulation. Accordingly, undesirable clotting can be avoided. This also means that the present bioadhesive formulation, when cured, has an anti-thrombogenic surface that prevents platelets formation. Advantageously, the present bioadhesive formulation is potentially useful for cardiovascular or vascular pathological conditions (e.g. ventricular or atrial septal defects). The antithrombotic agent may be or may comprise sebacic acid. Sebacic acid is a di-alkanoic acid containing 10 carbon atoms. Any other di-alkanoic acids or anticoagulants may be included as the antithrombotic agent, for example, any di-alkanoic acids containing 6 to 12 carbon atoms. The anticoagulants and/or antithrombotic agents may be water soluble and do not dissolve in polycaprolactone.

The present bioadhesive formulation may further comprise an anaesthetic agent. The anaesthetic agent can be used to relieve or for the relief of discomfort and/or pain during and/or after surgery. The present bioadhesive formulation is designable to have extended anaesthetic release. For example, the porosity of the polycaprolactone dendrimer can be tuned such that the bioadhesive, when cured by the stimulant, acts as a sponge that absorbs and/or expels fluids when subjected to stress and/or strain from surrounding tissues or environment, along with the release of the anaesthetic agent. The anaesthetic agent may be or may comprise bupivacaine. Other anaesthetic agents may include, for example, amylocaine, cocaine, levobupivacaine, mepivacaine, prilocaine, ropivacaine, etc.

Based on the above, the bioadhesive formulation may further comprise a hygroscopic additive, an antithrombotic agent, and/or an anaesthetic agent, according to various embodiments.

Accordingly, the present disclosure provides for a bioadhesive formulation that has already been described above according to various embodiments of the first aspect for use in (i) the prevention of thrombosis from tissue fixation and/or (ii) the relief of discomfort and/or pain during and/or after surgery.

The present disclosure also provides for the use of a bioadhesive formulation that has already been described above according to various embodiments of the first aspect in the manufacture of a porous bioadhesive composite for (i) the prevention of thrombosis from tissue fixation and/or (ii) the relief of discomfort and/or pain during and/or after surgery. The expression "bioadhesive composite" as used herein refers to the cured bioadhesive formulation.

The present disclosure further provides for a bioadhesive formulation that has already been described above according to various embodiments of the first aspect for use in therapy.

The present disclosure provides for a method of preventing thrombosis from tissue fixation. Embodiments and advantages described in the context of the present bioadhesive formulation are analogously valid for the method described herein for preventing thrombosis from tissue fixation, and vice versa.

As already described above, the present bioadhesive formulation can include the antithrombotic agent. This helps to prevent or eliminate thrombosis (including platelet clotting) of the applied bioadhesive. The method, accordingly, comprises implanting a bioadhesive formulation to a target site, wherein the bioadhesive formulation comprises an antithrombotic agent and a polycaprolactone dendrimer, wherein the polycaprolactone dendrimer has a dendrimer core and a plurality of polycaprolactone chains extending from the dendrimer core, wherein at least one of the polycaprolactone chains has an end which is covalently attached with a diazirine, and applying a stimulant to the bioadhesive formulation to convert the diazirine to a carbene and/or a diazoalkyl, thereby curing the bioadhesive formulation to form a porous bioadhesive composite having one or more surfaces incorporated with the antithrombotic agent.

Features and various embodiments of the present bioadhesive formulation, the polycaprolactone dendrimer, the dendrimer core, the plurality of polycaprolactone chains, the diazirine that is covalently attached, the stimulant, the carbene, the diazoalkyl, the antithrombotic agent, etc., have already been described above in various embodiments related to the first aspect.

The target site may refer to a tissue on which the present bioadhesive formulation is applied. The target site may be located in a patient's body. The target site may be or may comprise a vascular and/or cardiovascular tissue.

According to various embodiments of the method, applying the stimulant to may comprise exposing the implanted bioadhesive formulation to (i) electromagnetic radiation having one or more wavelengths from 315 nm to 1400 nm, and/or (ii) electromagnetic radiation having one or more intensities in the range of 1 mW·cm$^{-2}$ to 1000 mW·cm$^2$, and/or subjecting the implanted bioadhesive formulation to (iii) a current in the range of 1 mA to 100 mA and/or (iv) a voltage in the range of ±50 V. Further embodiments of the stimulant have already been described above in various embodiments related to the first aspect.

The present disclosure also provides for a method of relieving discomfort and/or pain during and/or after surgery. Embodiments and advantages described in the context of the present bioadhesive formulation are analogously valid for the method described herein for relieving discomfort and/or pain during and/or after surgery, and vice versa.

As already described above, the present bioadhesive formulation can include the anaesthetic agent. This helps to relieve discomfort and/or pain during and/or after surgery. The method, accordingly, comprises implanting a bioadhesive formulation to a target site, wherein the bioadhesive formulation comprises an anaesthetic agent and a polycaprolactone dendrimer, wherein the polycaprolactone dendrimer has a dendrimer core and a plurality of polycaprolactone chains extending from the dendrimer core, wherein at least one of the polycaprolactone chains has an end which is covalently attached with a diazirine, and applying a stimulant to the bioadhesive formulation to convert the diazirine to a carbene and/or a diazoalkyl, thereby curing the bioadhesive formulation to form a porous bioadhesive composite incorporated with the anaesthetic agent, wherein the anaesthetic agent is released from the porous bioadhesive composite when the porous bioadhesive composite is subjected to stress.

Features and various embodiments of the present bioadhesive formulation, the polycaprolactone dendrimer, the dendrimer core, the plurality of polycaprolactone chains, the diazirine that is covalently attached, the stimulant, the carbene, the diazoalkyl, the anaesthetic agent, etc., have already been described above in various embodiments related to the first aspect.

The target site may refer to a tissue on which the present bioadhesive formulation is applied. The target site may be located in a patient's body. The target site may be or may comprise a tissue wound.

According to various embodiments of the method, applying the stimulant may comprise exposing the implanted bioadhesive formulation to (i) electromagnetic radiation having one or more wavelengths from 315 nm to 1400 nm, and/or (ii) electromagnetic radiation having one or more intensities in the range of 1 mW·cm$^{-2}$ to 1000 mW·cm$^{-2}$, and/or subjecting the implanted bioadhesive formulation to (iii) a current in the range of 1 mA to 100 mA and/or (iv) a voltage in the range of ±50 V. Further embodiments of the stimulant have already been described above in various embodiments related to the first aspect.

In the present disclosure, a method of tissue fixation using the present bioadhesive formulation already described in various embodiments of the first aspect, is provided. Embodiments and advantages described in the context of the present bioadhesive formulation are analogously valid for the method described herein for tissue fixation, and vice versa.

The method of tissue fixation may comprise implanting a bioadhesive formulation to a tissue to be fixed, wherein the bioadhesive formulation comprises a polycaprolactone dendrimer having a dendrimer core and a plurality of polycaprolactone chains extending from the dendrimer core, wherein at least one of the polycaprolactone chains has an end which is covalently attached with a diazirine, and applying a stimulant to the bioadhesive formulation to convert the diazirine to a carbene and/or a diazoalkyl, thereby curing the bioadhesive formulation for tissue fixation.

Features and various embodiments of the present bioadhesive formulation, the polycaprolactone dendrimer, the dendrimer core, the plurality of polycaprolactone chains, the diazirine that is covalently attached, the stimulant, the carbene, the diazoalkyl, etc., have already been described above in various embodiments related to the first aspect.

According to various embodiments of the method, applying the stimulant may comprise exposing the implanted bioadhesive formulation to (i) electromagnetic radiation having one or more wavelengths from 315 nm to 1400 nm, and/or (ii) electromagnetic radiation having one or more intensities in the range of 1 mW·cm$^{-2}$ to 1000 mW·cm$^2$, and/or subjecting the implanted bioadhesive formulation to (iii) a current in the range of 1 mA to 100 mA and/or (iv) a voltage in the range of ±50 V. Advantageously, the application of the stimulant converts the diazirine into carbene and/or diazoalkyl which forms random non-specific and specific crosslinkages during curing of the bioadhesive formulation, respectively. This, accordingly, fixes the tissue and/or seals the tissue opening (e.g. wound). Further embodiments of the stimulant have already been described above in various embodiments related to the first aspect.

The bioadhesive formulation used in such a tissue fixation method may further include a hygroscopic additive. Various embodiments of the hygroscopic additive have already been described in various embodiments related to the first aspect.

In the present disclosure, a method of forming the present bioadhesive formulation is provided. The method may comprise mixing a polycaprolactone dendrimer precursor comprising one or more —OH and/or —COOH groups with a diazirine precursor in the presence of a mild base to form a mixture comprising a polycaprolactone dendrimer, wherein the diazirine precursor is represented by the formula:

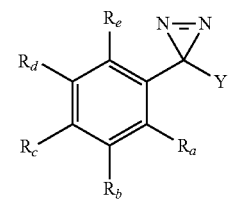

wherein at least one of $R_a$ to $R_e$ is hydrogen or —$C_{1-12}$ alkyl substituted with one or more halogens, wherein Y is hydrogen, halogen or —C$_{1-12}$ alkyl substituted with one or more halogens, filtering the mixture with a molecular sieve, and adding water to the filtered mixture to precipitate the polycaprolactone dendrimer, wherein the polycaprolactone dendrimer comprises a dendrimer core and a plurality of polycaprolactone chains extending from the dendrimer core, wherein at least one of the polycaprolactone chains has an end which is covalently attached with a diazirine via an ether linkage or an ester linkage, and wherein the diazirine converts to a carbene and/or a diazoalkyl when a stimulant is applied to the bioadhesive formulation. The ether linkage may be formed when a halogen of $R_a$ to $R_e$ reacts with the —OH group of the polycaprolactone dendrimer precursor. The ester linkage may be formed when a halogen of $R_a$ to $R_e$ reacts with the —COOH group of the polycaprolactone dendrimer precursor.

Embodiments and advantages described in the context of the present bioadhesive formulation are analogously valid for the method described herein for forming the present bioadhesive formulation, and vice versa.

Features and various embodiments of the present bioadhesive formulation, the polycaprolactone dendrimer, the dendrimer core, the plurality of polycaprolactone chains, the diazirine that is covalently attached, the stimulant, the carbene, the diazoalkyl, etc., have already been described above in various embodiments related to the first aspect.

Features and various embodiments of the polycaprolactone dendrimer precursor are already described above. The polycaprolactone dendrimer precursor may be a polycaprolactone dendrimer having at least one polycaprolactone chain with one or more —OH groups and/or —COOH groups, as already described above. The polycaprolactone dendrimer precursor may be synthesized from a polycaprolactone initiator. The polycaprolactone initiator may form the polycaprolactone dendrimer core. The polycaprolactone initiator may be a non-toxic precursor such as citric acid. The halogen in the present method may be fluorine, chlorine, bromine, etc.

In some embodiments of this method, the diazirine precursor may comprise

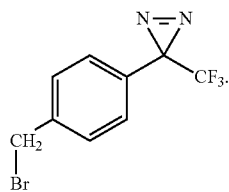

The polycaprolactone dendrimer precursor comprising one or more —OH and/or —COOH groups that is mixed with the diazirine precursor of this method, may be mixed in a molar ratio that depends on the number of —OH and/or —COOH groups that are present on the polycaprolactone dendrimer precursor. In some embodiments, mixing the polycaprolactone dendrimer precursor comprising one or more —OH and/or —COOH groups and the diazirine precursor may be in a molar ratio of 1:6, 1:5, 1:4, 1:3, 1:2 or 1:1, etc. The molar ratio may be used to adjust the amount of diazirine that is covalently attached to the polycaprolactone dendrimer, and this in turn controls the degree of curing (i.e. amount of crosslinking).

In various embodiments, mixing of the polycaprolactone dendrimer precursor with the diazirine precursor may be carried out without a solvent or with an anhydrous organic solvent. The term "anhydrous" as used herein in the present disclosure refers to the absence of water.

In various embodiments, the anhydrous organic solvent may comprise dichloromethane, diethyl ether, tetrahydrofuran, tetrahydropyran, 1,4-dioxane, benzene, toluene, ethyl tert-butyl ether, methyl tert-butyl ether, methyltetrahydrofuran, morpholine or diglyme. Other liquid ethers or dioxanes may also be used.

In various embodiments, the mild base may comprise silver oxide or pyridine. Advantageously, the use of mild base avoids decomposition of the diazirine precursor to be mixed, as strong bases (e.g. NaOH, NaH) can, for example, decompose aromatic bromine (e.g. diazirine bromine).

In various embodiments, the method may be carried out under inert atmosphere of nitrogen or argon.

In the present disclosure, another method of forming the present bioadhesive formulation is provided. The method may comprise mixing a polycaprolactone dendrimer precursor comprising one or more —OH and/or —COOH groups with a diazirine precursor in the presence of a mild base to form a suspension comprising a polycaprolactone dendrimer, wherein the diazirine precursor is represented by the formula:

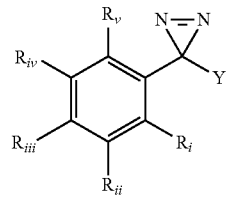

wherein at least one of $R_i$ to $R_v$ is hydrogen or —$R_{vi}$C(=O)—Z, wherein $R_{vi}$ is a bond or —C$_{1-12}$ alkyl- which is unsubstituted or substituted with one or more halogens, wherein Z is a halogen, wherein Y is hydrogen, halogen or —C$_{1-12}$ alkyl substituted with one or more halogens, and extracting the polycaprolactone dendrimer from the suspension, wherein the polycaprolactone dendrimer comprises a dendrimer core and a plurality of polycaprolactone chains extending from the dendrimer core, wherein at least one of the polycaprolactone chains has an end which is covalently attached with a diazirine via an ester linkage or an anhydride linkage, and wherein the diazirine converts to a carbene and/or a diazoalkyl when a stimulant is applied to the bioadhesive formulation. The ester linkage may be formed when —$R_{vi}$C(=O)—Z comprises an acyl halide that reacts with the —OH group of the polycaprolactone dendrimer precursor. The anhydride linkage may be formed when —$R_{vi}$C(=O)—Z comprises an acyl halide that reacts with the —COOH group of the polycaprolactone dendrimer precursor.

Embodiments and advantages described in the context of the present bioadhesive formulation are analogously valid for this other method described herein for forming the present bioadhesive formulation, and vice versa.

Features and various embodiments of the present bioadhesive formulation, the polycaprolactone dendrimer, the dendrimer core, the plurality of polycaprolactone chains, the diazirine that is covalently attached, the stimulant, the carbene, the diazoalkyl, etc., have already been described above in various embodiments related to the first aspect.

Features and various embodiments of the polycaprolactone dendrimer precursor already described above in the earlier method, are applicable to the polycaprolactone dendrimer precursor of this other method as well. The halogen in the present method may be fluorine, chlorine, bromine, etc.

In some embodiments of this method, the diazirine precursor may comprise

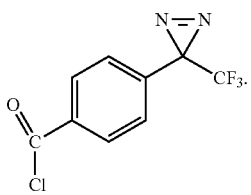 [SMILES: O=C(Cl)c1ccc(C2(C(F)(F)F)N=N2)cc1]

The polycaprolactone dendrimer precursor comprising one or more —OH and/or —COOH groups that is mixed with the diazirine precursor of this method, may be mixed in a molar ratio that depends on the number of —OH and/or —COOH groups that are present on the polycaprolactone dendrimer precursor. In some embodiments, mixing the polycaprolactone dendrimer precursor comprising one or more —OH and/or —COOH groups and the diazirine precursor may be in a molar ratio of 1:6, 1:5, 1:4, 1:3, 1:2 or 1:1, etc. The molar ratio may be used to adjust the amount of diazirine that is covalently attached to the polycaprolactone dendrimer, and this in turn controls the degree of curing (i.e. amount of crosslinking).

In various embodiments, mixing of the polycaprolactone dendrimer precursor with the diazirine precursor may be carried out without a solvent or with an anhydrous organic solvent.

In various embodiments, the anhydrous organic solvent may comprise diethyl ether. Other anhydrous organic solvents may include, dichloromethane, tetrahydrofuran, 1,4-dioxane, benzene, toluene, ethyl tert-butyl ether, methyl tert-butyl ether, methyltetrahydrofuran, morpholine, diglyme, tetrahydropyran, etc. Other liquid ethers or dioxanes may also be used.

In various embodiments, the mild base may comprise silver oxide or pyridine. The advantage of using a mild base as described above in the earlier method, applies to the mild base of this method. Pyridine is also advantageous as it can be removed entirely by any convenient separation process, such as water extraction, vacuum evaporation, etc. Other water-soluble mild bases or a mild base that is soluble in an organic solvent can also be used. A non-limiting example is alkanamines.

In various embodiments, extracting the polycaprolactone dendrimer may comprise (i) adding aqueous HCl, aqueous $NaHCO_3$, brine and water to the suspension or (ii) mixing the suspension with ethyl acetate to form a mixture and adding aqueous HCl, aqueous $NaHCO_3$, and brine to the mixture.

In various embodiments, the mixture may be further dried on a drying agent after adding the aqueous HCl, the aqueous $NaHCO_3$, and the brine. The drying agent may comprise $Na_2SO_4$.

Embodiments and advantages described for the present bioadhesive formulation in the first aspect are analogously valid for embodiments and features of any subsequent aspects described herein, for example, the uses and methods of forming of the present bioadhesive formulation, and vice versa.

While the methods described above are illustrated and described as a series of steps or events, it will be appreciated that any ordering of such steps or events are not to be interpreted in a limiting sense. For example, some steps may occur in different orders and/or concurrently with other steps or events apart from those illustrated and/or described herein. In addition, not all illustrated steps may be required to implement one or more aspects or embodiments described herein. Also, one or more of the steps depicted herein may be carried out in one or more separate acts and/or phases.

EXAMPLES

The present disclosure relates to bioadhesives produced from synthetic organic components. Particularly, the present disclosure relates to biodegradable polymeric systems that are usable as adhesives, sealants, and drug eluting coatings, for application on soft and wet tissue surface.

The method of preparing the polymer bioadhesive (sealant) disclosed herein describes a water-free and/or solvent-free liquid adhesive, which crosslinks rapidly under external stimulation (heat, ultraviolet irradiation, voltage, etc.) into an elastomeric foam that can bond hydrated surfaces. Features of the present bioadhesive include (1) absorption, dispersion, or both, of surface water on hydrated substrates that imparts a temporary reduction of surface hydration to allow substrate covalent crosslinking, (2) programmable volume expansion from 10% to 300% that allows complete surface coverage and filling of substrate voids, through generation of open or closed cell gas-filled foams, and (3) non-specific, indiscriminate crosslinking of substrate Q-H (where Q=C, N, O, or S) bonds via energy activated diazo functional groups.

The present bioadhesives, their uses and methods of forming the present bioadhesives, are described in detail, by way of the non-limiting examples set forth below.

Example 1A: Advantages and Improvements Over Conventional Cyanoacrylate Bioadhesives The present bioadhesive is an improvement over conventional cyanoacrylate bioadhesives (e.g. Ethicon Dermabond).

The degradation products of Dermabond induce inflammation, and Dermabond is therefore limited to topical and skin applications. Hygroscopic additives cannot be added to cyanoacrylates as they trigger polymerization. That is to say, it is difficult to exclude trace amounts of moisture that can initiate polymerization of cyanoacrylate, when hygroscopic additives are used in combination with cyanoacrylates.

Meanwhile, degradation products of the present polycaprolactone bioadhesives are bioresorbable. The implanted surfaces of cured polycaprolactone bioadhesives in animal models, demonstrated herein, exhibited no outstanding inflammatory reactions. Moreover, polycaprolactone polymers are listed under the category of "Generally Recognized as Safe (GRAS)" by the US FDA.

Example 1B: Advantages and Improvements Over Conventional Fibrin Adhesives

The present bioadhesive is an improvement over conventional fibrin adhesives (e.g. Baxter Tisseel).

The Young's modulus of fibrinogen adhesives are limited to 10 kPa to 30 kPa regardless of the fibrinogen or thrombin concentration, in fibrin gels. This renders them relatively weak and they are unable to match the material properties of many soft tissues and soft substrates, limiting their use to hemostatic purposes.

In contrast, the present polycaprolactone bioadhesives has Young's modulus, storage modulus, loss modulus, and tan delta (a viscoelasticity parameter), that can be tuned. For instance, the Young's modulus of the present polycaprolactone bioadhesive can be tuned easily from 1 kPa to 300 kPa.

Additionally, hygroscopic additives do not improve adhesion of conventional fibrin adhesives, as the fibrin adhesives are already dissolved in aqueous solutions. Moreover, fibrin adhesives have difficulty (i) dissolving or cannot dissolve in organic solvents, and (ii) forming into aqueous-free and/or solvent-free formulations.

Example 1C: Advantages and Improvements Over Conventional Polyethylene Glycol (PEG) Sealants The present bioadhesive is an improvement over conventional PEG sealants (e.g. CoSeal and DuraSeal).

Conventionally, PEG sealants consist of chemically functionalized linear or branched PEG molecules. They can be crosslinked upon mixing, through chemical crosslinking, or upon irradiation of light by photo-crosslinking of PEGs capped with photo-reactive elements such as acrylate groups, to form a hydrogel adhesive. However, PEG sealants require dry surfaces for good adhesion and have a swell ratio of up to 400% of its original volume. The latter means that more caution is required when applying PEG sealants to closed spaces to avoid pressure build up on surrounding tissues (e.g. nerve compression).

PEG sealants also require reconstitution from dry components and only have a 2 hour stability after reconstitution. CoSeal's PEG sealant has demonstrated skin sensitization in animals, and Duraseal's blue dye may be associated with allergic responses. On the other hand, the present polycaprolactone bioadhesive, being hydrophobic, does not have such a large swell ratio, and no reconstitution of polycaprolactone is necessary.

Further, hygroscopic additives do not improve the wet adhesion of PEG sealants since they are already prepared and dissolved in aqueous solutions (reconstituted).

Example 1D: Advantages and Improvements Over Conventional Acrylate Pressure Sensitive Adhesive (PSA) Patches The present bioadhesive is an improvement over conventional acrylate PSA patches (e.g. DURO-TAK and GELVA PSA patches). Such acrylate PSA patches work only on clean, dry surfaces, and the surfaces are limited to skin and topical applications. Such acrylate based bioadhesives are also limited in their forms, i.e. as films or patches.

In contrast, the present polycaprolactone bioadhesives can stick to wet and hydrated surfaces. They can be formulated into liquid formulations (for syringe, spray, brush applicators), patches, films, and rheological transitioning viscoelastic formulations (thermo-gelling).

Further, hygroscopic additives do not improve adhesion of acrylate PSA patches as the acrylate adhesive is too viscous to allow water penetration.

Example 1E: Advantages and Improvements Over Polyurethane Bioadhesives

The present bioadhesive is an improvement over polyurethane bioadhesives.

Polyurethanes have three challenges to overcome for use as a bioadhesive, and they include (1) prolonged set time, (2) ether-based polyurethanes are not readily biodegradable, and (3) toxicity and carcinogenicity of its degradation products. The present polycaprolactone bioadhesive circumvents such issues due to its synthesis method, its method of crosslinking, and is a superior bioadhesive over polyurethane bioadhesive in view of the above issues.

Example 1F: Advantages and Improvements Over Conventional Protein Glues

The present bioadhesive is an improvement over conventional protein glues (e.g. Bioglue, Cryolife, Kennesaw).

GRF/GRFG glues (gelatin resorcinol formaldehyde/glutaraldehyde), also known as "French glue", is a two-component glue consisting of (1) a mixture of gelatin and resorcinol, and (2) formaldehyde or a combination of formaldehyde and glutaraldehyde as the polymerizing agent. Despite being used for many years, particularly in Europe, the presence of formaldehyde, as a residue of unreacted aldehydes or as a degradation product, is a concern due to its possible mutagenicity, carcinogenicity, hypersensitivity, and local tissue necrosis. On the other hand, the US FDA already classifies polycaprolactone polymers under the GRAS list, which implies that the present polycaprolactone bioadhesive is cleared of such issues.

Example 1G: Advantages and Improvements Over 3,4-Dihydroxyphenylalanine (DOPA) Based Mussel Adhesive Proteins The present bioadhesive is an improvement over DOPA based mussel adhesive proteins.

DOPA based adhesives are dependent on different oxidation agents such as horseradish peroxide, hydrogen peroxide, sodium periodate and mushroom tyrosinase. Such oxidizing reagents result in acute or chronic inflammation. Also, its synthetic production is complex and not conveniently scalable. The present polycaprolactone bioadhesive, however, does not require oxidizing agents and its synthetic methods are simple and straightforward.

Example 1H: Other Advantages and Improvements of the Present Polycaprolactone Bioadhesives The present polycaprolactone bioadhesives expand moderately during curing. The polycaprolactone bioadhesives expand when curing due to the liberation of nitrogen, thus having advantages as a sealant having a water impenetrable surface, or for clogging perforated organs (e.g. pneumothorax). Meanwhile, conventional bioadhesives tend to contract or shrink upon curing. Compared with PEG sealants, PEG sealants only swell after curing due to absorption of water from the tissues. The absorption happens because the PEG sealants are hydrophilic matrixes before and after curing. The water absorption of PEG sealants cannot be controlled as it depends on many factors, including surrounding tissues, hydration presence, location, etc.

The present polycaprolactone bioadhesives are transparent to visible light wavelengths, before and even after curing, thus allowing observation of the underlying substrate (e.g. sealed tissue wound).

A combination of the present polycaprolactone bioadhesives and hygroscopic additives advantageously increases adhesion and storage modulus of the present polycaprolactone bioadhesives.

Example 2A: One-Pot Synthesis Method 1

Diazirine grafting onto the —OH and —COOH pendant functional groups of a polycaprolactone polyol dendrimer was achieved by two methods. The first method is described as follows and the second is described in example 2B.

In the first method, a $S_N2$ reaction between alcohols and halides in the presence of a mild base, is utilized for diazirine conjugation. The diazirine conjugation reaction is described in scheme 1 below.

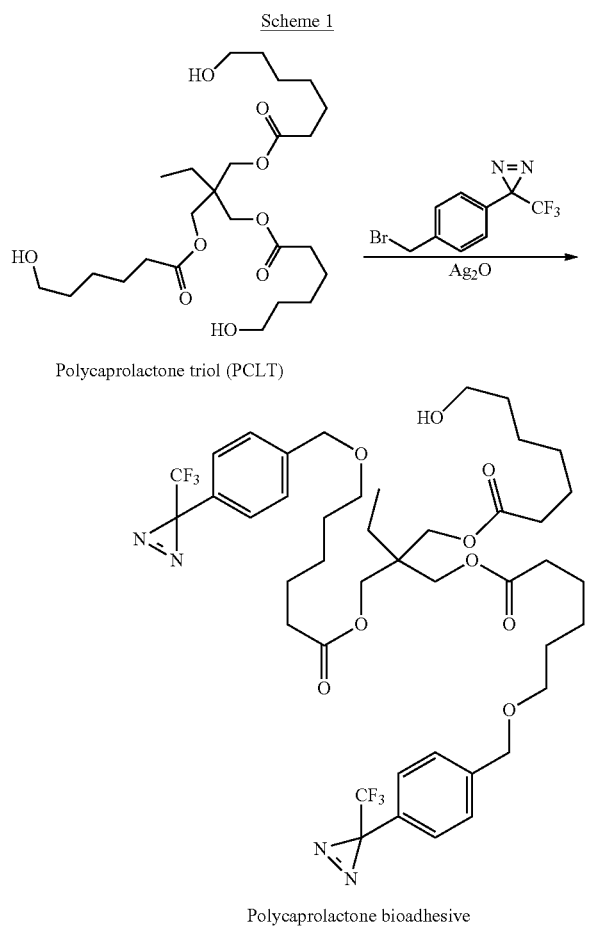

Polycaprolactone triol (PCLT)

Polycaprolactone bioadhesive

In scheme 1, the polycaprolactone (PCLT) triol (left structure) is chemically modified with bromo-diazirine (in a 2:1 molar ratio of diazirine:PCLT) based on a Williamson-ether reaction in the presence of a mild base silver oxide ($Ag_2O$). As the reaction may be water sensitive, all the components used for the reaction (including any solvents) should be dried (or free of water) prior to the reaction.

Freshly prepared silver oxide ($Ag_2O$) was used instead of strong bases, such NaOH or NaH, as the bromide scavengers. This is because strong bases can decompose aromatic bromine (diazirine bromine in this case) and thus have to be avoided. The molar ratio between a diazirine precursor (e.g. bromo-diazirine) and other reactants can be adjusted according to the number of pendant —OH and/or —COOH groups on the polycaprolactone chains, where each one of the pendant groups reacts with one molar equivalent of diazirine precursor (scheme 1).

The reaction was carried out either in neat conditions (no solvents) or with the use of organic solvents, e.g. 1,4-dioxane, benzene or toluene, in the presence of freshly prepared $Ag_2O$. Other polar aprotic solvents (e.g. dichloromethane (DCM) or tetrahydrofuran (THF)) are usable.

The term "aprotic" as used herein refers to substances that are unable to donate a hydrogen or $H^+$ ion. If volatile solvents are to be used (e.g. DCM or THF), the reaction should be placed under reflux. Inert atmosphere (nitrogen or argon) and the use of molecular sieves may be necessary for eliminating water from the reaction mixture. The reaction was carried out for 48 hours to 96 hours at room temperature. The product was then filtered or centrifuged from molecular sieves (e.g. 4 angstrom, aluminosilicate minerals or zeolites based molecular sieves) and AgBr is formed as the other reaction product. 1,4-dioxane is a preferred solvent because its water miscibility allows the precipitation of the diazirine-dendrimer in water, thereby acting as a non-solvent after the reaction is completed. In this particular case, the dioxane solution of the product is added to water and further filtered and freeze dried. If more volatile solvents are used (e.g. DCM or THF), the filtered product can be isolated by solvent evaporation.

Possible molecules for diazirine conjugation include polycaprolactone polyol (e.g. polycaprolactone diol, polycaprolactone triol, polycaprolactone tetrol, polycaprolactone pentol, polycaprolactone hexol), polyethylene glycol (PEG), polyvinyl alcohol (PVA), glycerol, citric acid and other polymers, prepolymers and monomers having one or more —OH and/or —COOH groups. The polycaprolactone to precursor for forming the polycaprolactone polyol dendrimer may be a liquid (rheological tan delta more than 1) at any temperature from 10 to 60° C. and has a number average molar mass from 300 to 3000 Da.

In the present disclosure, prepolymers refer to crosslinked polymers that may be dissolved in organic solvents or melted to exist as a neat liquid. For example, POCS (polyoctanediol citrate/sebacate), and PGS (poly glycerol sebacate), may go through two stages of curing. The first stage involves the prepolymer, which may be soluble in organic solvents or melted into a neat liquid. The second curing stage (thermocuring or photocuring) may result in a crosslinked biorubber that may not be dissolved or melted. The PCLT-D70 may be considered a prepolymer.

Example 2B: One-Pot Synthesis Method 2

The second method deals with conjugation of diazirine to a polymeric dendrimer via —COOH groups. If a diazirine acid containing one or more COOH groups is used, it can still be conjugated to a polymeric dendrimer having —OH and/or —COOH groups. A relatively high concentration of pendant —COOH groups on the dendrimer present possibilities for further functionalization with diazirine. The second method is represented via schemes 2 and 3 as set forth below.

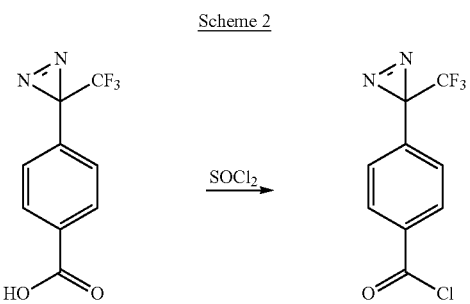 [SMILES: O=C(O)c1ccc(C2(C(F)(F)F)N=N2)cc1 ; "SOCl2" ; O=C(Cl)c1ccc(C2(C(F)(F)F)N=N2)cc1]

Scheme 2

In the first step, as denoted by scheme 2 which shows diazirine acyl chloride formation from the use of $SOCl_2$, 4-[3-(trifluoromethyl)-3H-diazirine-3-yl] benzoic acid (diazirine acid) was converted into an acyl chloride via nucleophilic addition-elimination with a chloride ion (e.g. from thionyl chloride, $SOCl_2$). The reaction can take place for 15 hours under dark conditions (i.e. in the absence of light). The reaction can also take place in the presence of phosphorus pentachloride ($PCl_5$) or phosphorus trichloride ($PCl_3$).

In the second step, denoted by scheme 3 below, the reactive diazirine acyl chloride that is produced via scheme 2, forms either ester bonds with the —OH groups or anhydride bonds with the —COOH groups of the polymeric dendrimer. An example of the conjugation reaction between the diazirine acyl chloride and a polycaprolactone triol is depicted in scheme 3 below. A mild base of pyridine is used.

Scheme 3

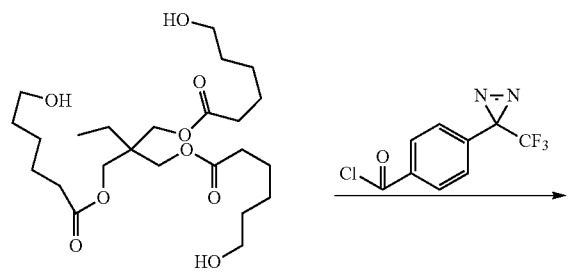

Polycaprolactone triol (PCLT)

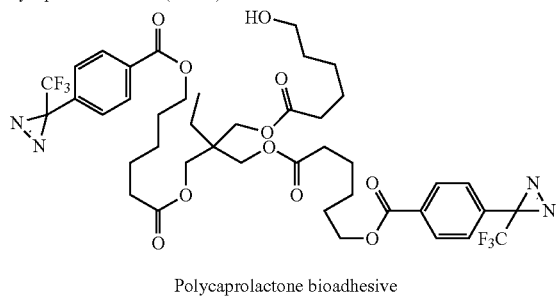

Polycaprolactone bioadhesive

In scheme 3, the diazirine acyl chloride reaction with polycaprolactone triol (with 3 pendant —OH groups, and molar ratio of diazirine acyl chloride:PCLT is 2:1) results in an ester linkage between the conjugated diazirine and the polycaprolactone dendrimer.

Possible molecules for diazirine conjugation include various polycaprolactone polyol, for example, polycaprolactone diol, polycaprolactone triol, polycaprolactone tetrol, polycaprolactone pentol, polycaprolactone hexol. The polycaprolactone precursor for forming the polycaprolactone polyol dendrimer may be a liquid (rheological tan delta more than 1) at any temperature from 10 to 60° C. and has a number average molar mass from 300 to 3000 Da.

Example 3: Crosslinking Via Unique Methods of Curing and Near-Infrared Activation Depending on the UVA intensity, joules dose, and wavelength (e.g. 340 nm to 390 nm) used, the diazirine can be activated to have transient carbene chemistry or converted into a diazoalkylating agent.

With transient carbene chemistry, the carbene can instantly react with any neighboring Q-H (where Q=C, N, O, or S) bonds for crosslinking. This means that the crosslinking is non-specific, and the carbene can be crosslinked to additives, precursor polymers, water, dissolved aqueous small molecules, substrates, etc.

For specific crosslinking, the diazoalkylating agent converted from the conjugated diazirine through suitable optical parameters can be used. Such optical parameters, as shown in scheme 4 below, favor the formation of a diazoalkylating agent and include low intensity UVA, low joule doses, longer UVA wavelengths, etc. Low intensity UVA may be UVA having an intensity ranging from 0.1 to 100 $mW \cdot cm^{-2}$. Low joule doses may include pulse width modulation or duty cycle ranging from 0.1 to 0.5 and/or with light pulses ranging from $10^3$ to $10^9$ Hz, more preferably $10^7$ to $10^9$ Hz, at UVA wavelengths. Longer UVA wavelengths may range from 370 nm to 400 nm. Visible wavelength activation may be from 400 nm to 500 nm.

Triplet sensitization may also be used for converting the conjugated diazirine into the diazoalkylating agent. Triplet sensitization allows visible wavelength excitation, which is a process in which the molecule of interest is not directly excited. Instead, the excitation involves an auxiliary molecule, referred to as the sensitizer. After excitation to the singlet state, the sensitizer spontaneously converts, through intersystem crossing (ISC), to a triplet, usually with high yields. It then transfers its energy to the diazirine in a triplet energy transfer (TET) step. Triplet photo-sensitizers may be available in the visible range from 400 nm to 500 nm.

Scheme 4

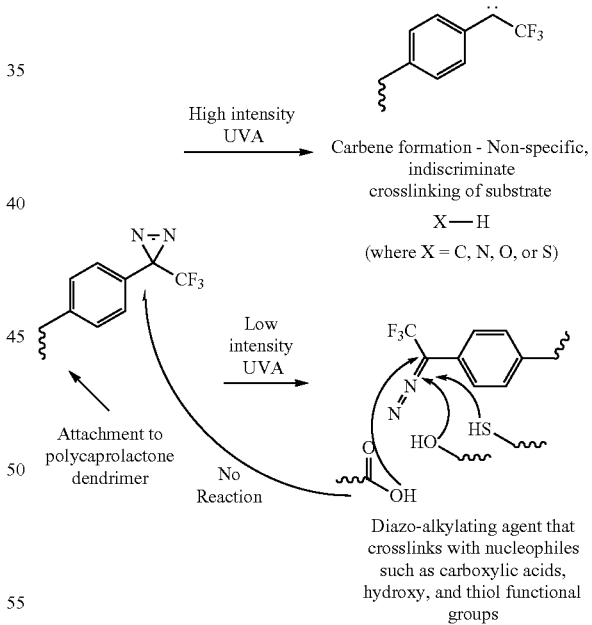

Scheme 4 demonstrates the use of variable UVA intensity that provides for specific and non-specific crosslinkings. With high intensity UVA, carbene instantly forms and this leads to non-specific crosslinking with any nearby molecules containing Q-H bonds (wherein Q=C, N, O, or S), including those of solvents, additives, and precursors for forming the polymeric dendrimers. Low intensity UVA, in contrast, converts the diazirine into a diazo isomer that crosslinks selectively with nucleophilic functional groups present on tissue surfaces.

For achieving both types of crosslinking, a two-photon absorption (e.g. UVA containing both high and low intensities) was employed. The two-photon absorption provides for the two types of diazirine activation, and allows for controlling the ratio of carbene/diazoalkyl functional groups. The two-photon absorption also allows using near-infrared wavelengths of 680 nm to 730 nm, which is located within the tissue optical window (i.e. 650 nm to 750 nm), where activation at these wavelengths allows subcutaneous activation of polycaprolactone bioadhesives.

Example 4A: Polycaprolactone Bioadhesive with Hygroscopic Additives

Polycaprolactone bioadhesive with 70% grafted diazirine (molar ratio of —OH:diazirine is 3:7), labeled as PCLT-D70 formulation, was mixed with citric acid (CA) in order to produce a bioadhesive with a hygroscopic component, as seen in FIG. 1A.

The hygroscopic agent absorbs and reduces the interfacial water on the tissue surface, further enhancing the contact between the carbene pendant groups of PCLT-D70 and the tissue. This in turn enhances tissue adhesion, even in a highly hydrated physiological environment. Prior to ex vivo tissue evaluation of this concept, raw PCLT-D70 with the citric acid additive was analyzed for rheological properties upon UV activation as shown in FIG. 1B.

Example 4B: Polycaprolactone Bioadhesives with Hygroscopic Additives for Bonding to Wet Tissue Surfaces Significantly faster increase of storage modulus G' was observed for the composite formulations within 1 min of UV activation (the exact storage modulus G' values are displayed in FIG. 1B). As a result of higher crosslinking density due to the presence of hygroscopic additives (citric acid), G' increased from 7 kPa up to 660 kPa after 2 mins of UV activation.

Example 4C: Ex Vivo Experiment with Rat Liver

Figure 2:
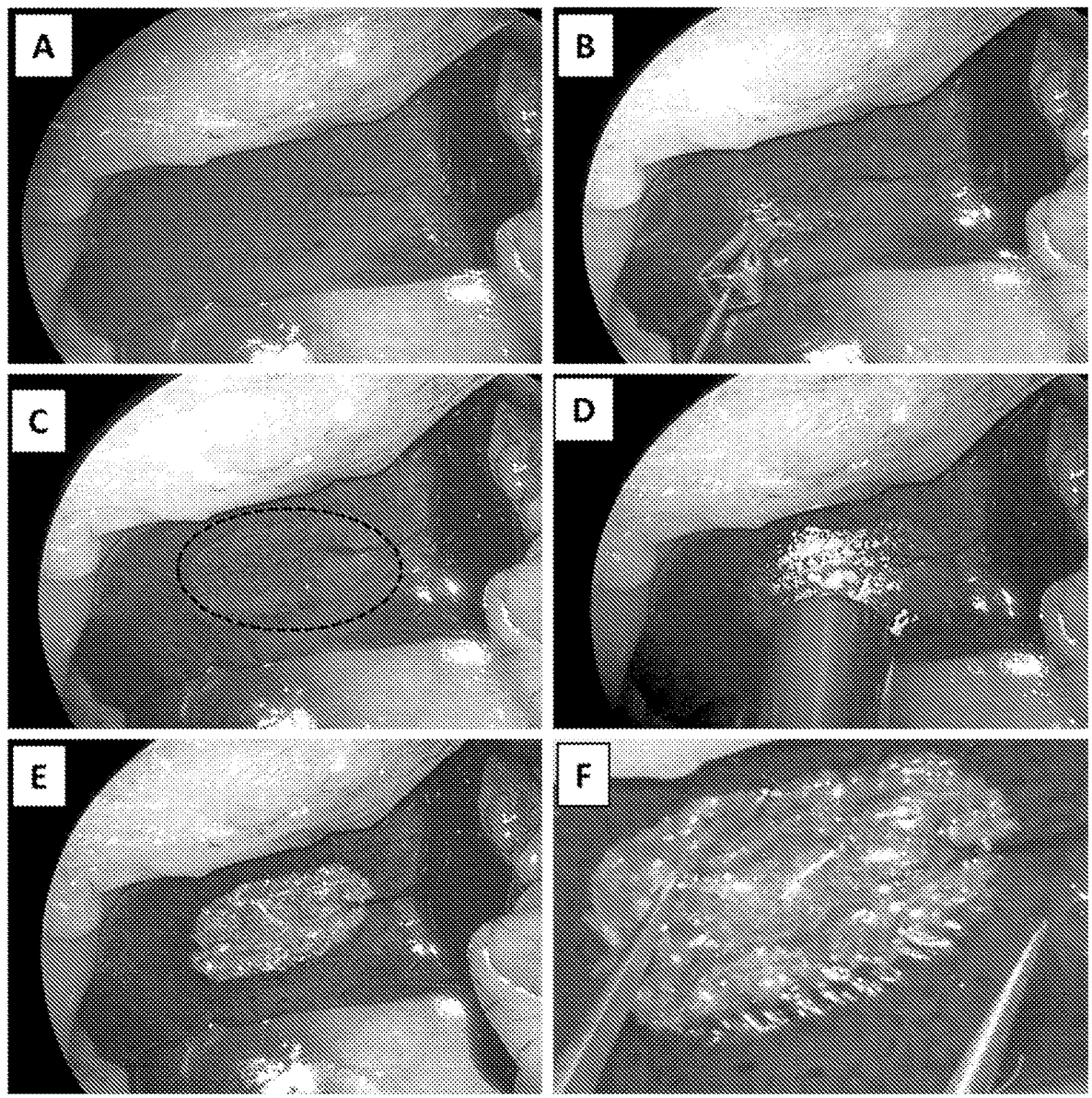
FIG. 2A shows the crosslinking of a PCLT-D70/CA composite (hygroscopic additive of citric acid and 70% of grafted diazirine) on cadaveric rat liver.
FIG. 2B shows the crosslinking of a PCLT-D70/CA composite (hygroscopic additive of citric acid and 70% of grafted diazirine) on cadaveric rat liver.
FIG. 2C shows the crosslinking of a PCLT-D70/CA composite (hygroscopic additive of citric acid and 70% of grafted diazirine) on cadaveric rat liver.
FIG. 2D shows the crosslinking of a PCLT-D70/CA composite (hygroscopic additive of citric acid and 70% of grafted diazirine) on cadaveric rat liver.
FIG. 2E shows the crosslinking of a PCLT-D70/CA composite (hygroscopic additive of citric acid and 70% of grafted diazirine) on cadaveric rat liver.
FIG. 2F shows the crosslinking of a PCLT-D70/CA composite (hygroscopic additive of citric acid and 70% of grafted diazirine) on cadaveric rat liver.

Ex vivo experiment was performed with cadaveric rat liver freshly exposed for bioadhesive, sealant, and coating applications. The size of the liver surface (about 4 cm$^2$, see FIG. 2A) allowed application of the PCLT-D70/citric acid composite formulations by spreading a thin layer over the hydrated tissue surface (FIG. 2B). The bioadhesive surface (FIG. 2C) was crosslinked with exposure to UV light (70 mW·cm$^{-2}$ for 2 mins, see FIG. 2D) and the layer of solidified foam composite is shown in FIG. 2E. Qualitative measurements of adhesion stress, by stressing the matrix with tweezers (about 50 g shear force over 3 mm$^2$, see FIG. 2F), suggest adhesion strengths of more than 10 kPa.

Example 5: Polycaprolactone Bioadhesive with Hygroscopic Additives for Mimicking Bone Material Properties The present polycaprolactone bioadhesives were also demonstrated for tendon and bone tissue fixation. The polycaprolactone bioadhesives used for tendon and bone tissue fixation were formulated by mixing PCLT-D50 and PCLT-D70 bioadhesives with hygroscopic additives of hydroxyapatite (HA) nanoparticles in predetermined concentrations. Diazirine conjugation (percentages 50% and 70%) of the polycaprolactone pendant —OH groups on the PCLT triol (precursor) and the concentration of hydroxyapatite nanoparticles enhanced the adhesive strength of the present bioadhesive due to an increase in crosslinking density. The prepared polycaprolactone bioadhesives of this example with HA hygroscopic additives and pure polycaprolactone bioadhesives were analysed for their rheological properties and the results are shown in FIGS. 3A and 3B.

Figure 3:
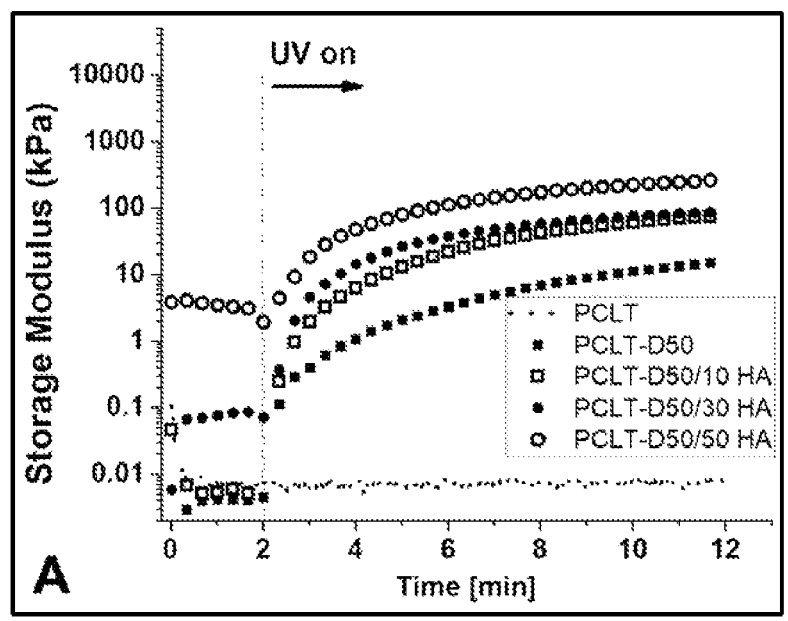
FIG. 3A shows the rheological G' values measured for PCLT-D50 composites having hydroxyapatite nanoparticles as the hygroscopic additive with UVA activation (120 mW·cm$^{-2}$), wherein the hygroscopic additive is at 0% w/w, 10% w/w, 30% w/w, and 50% w/w. A PCLT control is also compared to demonstrate the control has no crosslinking ability.
FIG. 3B shows the rheological G' values measured for PCLT-D70 composites having hydroxyapatite nanoparticles as the hygroscopic additive with UVA activation (120 mW·cm$^{-2}$), wherein the hygroscopic additive is at 0% w/w, 10% w/w, 30% w/w, and 50% w/w. The highest shear storage modulus of 27 MPa was attained with PCLT-D70 and 50% w/w hydroxyapatite nanoparticles, which is 40% to 60% of the shear modulus of trabecular bone (50-70 MPa). A PCLT control is also compared to demonstrate the control has no crosslinking ability.
Figure 3:
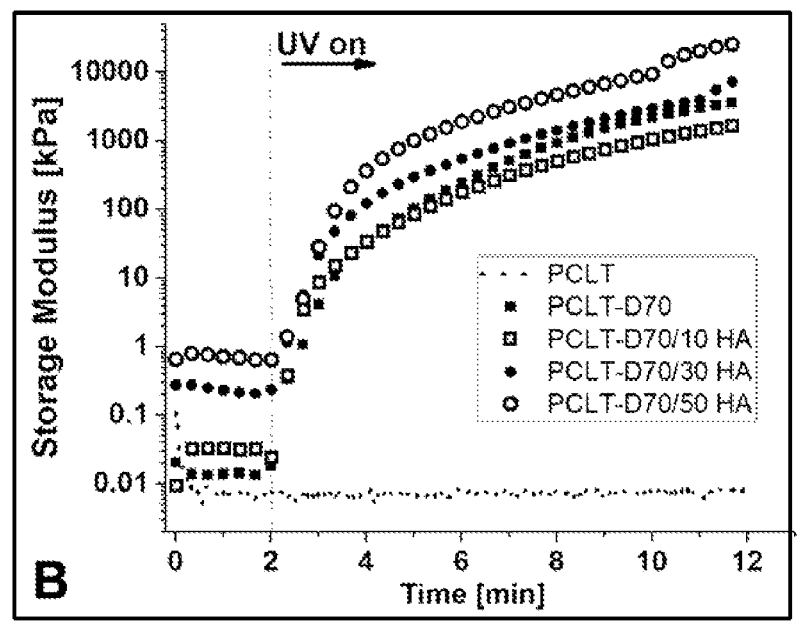

The shear storage modulus G' value of 15 kPa for PCLT-D50 bioadhesive increased gradually with concentration of HA to reach a maximum G' value of 270 kPa as seen in FIG. 3A. This spans the range of tendons with shear moduli of 50 kPa to 200 kPa. In case of PCLT-D70, an increase of G' value was even more significant due to increased crosslinking density caused by UVA activation. FIG. 3B shows an increase from 3 MPa for neat PCLT-D70 up to 27 MPa measured for PCLT-D70/HA (50%), which is 40% to 60% of the shear modulus of trabecular bone (50 MPa to 70 MPa).

Figure 4:
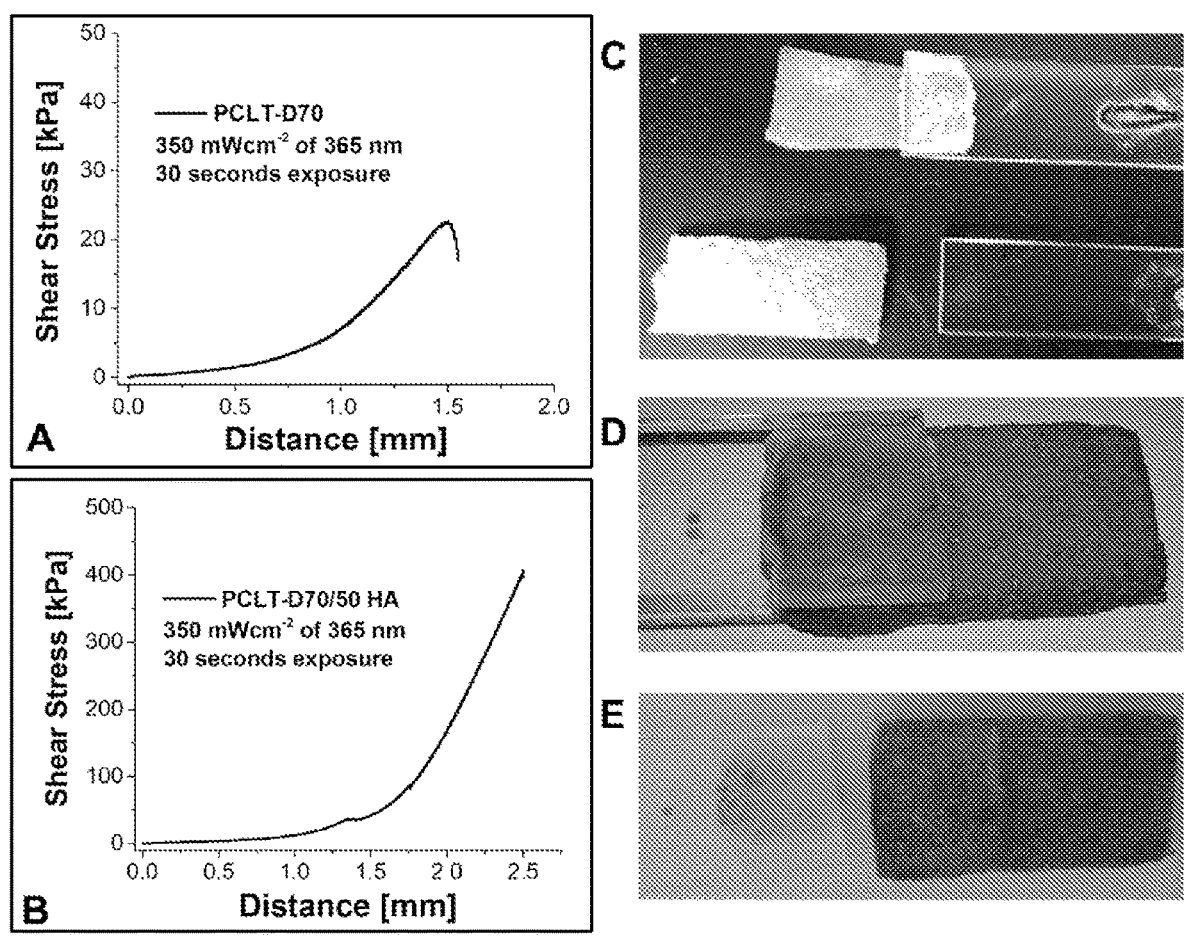
FIG. 4A shows the lap-shear adhesion test results.
FIG. 4B shows the lap-shear adhesion test results.
FIG. 4C shows a digital photograph of bone samples adhered to poly(methyl methacrylate) (PMMA) sheets used for demonstrating the lap-shear adhesion test.
FIG. 4D shows a digital photograph of bone samples adhered to PMMA sheets used for demonstrating the lap-shear adhesion test.
FIG. 4E shows the cohesive failure of the PMMA sheets and bone after adhesion. The cohesive failure demonstrated that the bone was not damaged after bonding failure.

Example 6: Polycaprolactone Bioadhesive with Hygroscopic Additives for Strong Adhesion to Bone Tissues This example demonstrates the assessment of the potential of PCLT-D70 bioadhesive with hygroscopic additives of hydroxyapatite (HA) as a bone adhesive, sealant, or coating. The ex vivo tests were performed with freshly cut bone plates adhered to poly(methyl methacrylate) (PMMA) substrates, which is a commonly implanted medical plastic, as seen in FIGS. 4C and 4D.

The adhesion strengths of both pure PCLT-D70 and PCLT-D70/HA (50%) composite were measured. When UVA intensity was activated for 30 sec at 350 mW·cm$^{-2}$, the pure PCLT-D70 control showed moderate adhesion strength measured for soft tissue (about 20 kPa, bone tissue ex vivo measurements, see FIG. 4A). The crosslinking activation with UV power (350 mW·cm$^{-2}$) of PCLT-D70/HA (50%), however, reached a significantly higher value that remained undetermined as the adhesion strength exceeded that of the 50 N force cell (FIG. 4B), thereby exceeding an adhesion strength of 125 kPa. In other words, the adhesion strength of PCLT-D70/HA (50%) exposed to UV power (350 mW·cm$^2$) exceeds the adhesion strength of cyanoacrylates (e.g. Dermabond) bioadhesives.

Example 7: Bulk Synthesis of Polycaprolactone Triol/Tetrol Grafted Diazirine (Bioadhesives V, VI and VII)

The synthetic procedure shown in scheme 5 below yields the elastic polycaprolactone bioadhesives at a cost of USD 20 per gram, on the basis of the materials shown in that scheme. The limiting starting reagent, in terms of cost, is the diazirine intermediate I, which accounts for 99.9% of the cost for laboratory production. To lower the cost of production to less than USD 1 per gram, pilot scale reaction methodologies that allow 10 to 100 times scale up with minimal changes have to be designed. The dendrimer bioadhesive VI is derived based on 45 wt % diazirine III and 55 wt % polycaprolactone dendrimer IV. The polycaprolactone triol/tetrol dendrimers IV are used in the manufacturing of polyurethane, bulk quantities at less than USD 1 per kg are therefore readily available.

Scheme 5

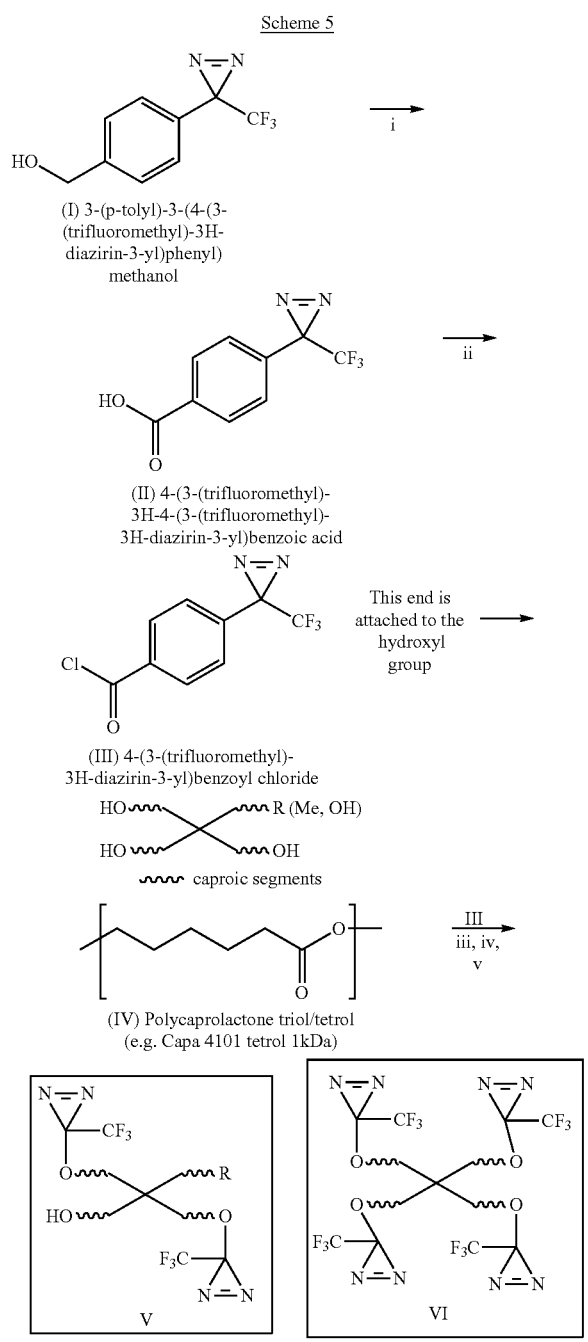

Scheme 5 shows the scaled-up synthesis of present polycaprolactone bioadhesives. The reagents used in steps (i) to (iii) are (i) a base and KMnO$_4$, (ii) DCM and SOCl$_2$, and (iii) diethyl ether and pyridine, respectively. Steps (i) to (v) of scheme 5 are described in detail as follows.

Step (i)—Oxidation of Diazirine Benzyl Alcohol I to Diazirine Benzoic Acid II:

76.26 grams of the diazirine benzoic acid II was prepared from 76.5 grams of the diazirine benzyl alcohol I (with a 93% yield). The diazirine benzyl alcohol was stirred in 0.5 L of aqueous NaOH (6.58 gram) and 100 mL of dioxane, all placed in a 1 L flask immerced in water bath. Further, 80.7 grams of KMnO$_4$ powder was added in small portions (5 to 10 grams) while maintaining the temperature at less than 40° C. The contents were left to stir for 3 more hours. Excess KMnO$_4$ was decolorized by adding Na$_2$SO$_3$ until the pink color disappeared. Then, the brown precipitate of MnO$_2$ was filtered and thoroughly washed with water, the filtered solution was acidified with H$_2$SO$_4$ (e.g. 20% H$_2$SO$_4$) until pH is about 1. The product, in the form of a white precipitate, was collected on a filter, thoroughly washed with water and dried in a dessicator, yielding 76.26 grams (constant weight, 93% yield) of the diazirine benzoic acid.

Step (ii)—Conversion of the Diazirine Benzoic Acid II to its Acyl Chloride III:

76 grams of the diazirine benzoic acid was converted to its acyl chloride (84 grams, at least 95%). All this acyl chloride was used for esterification of the Capa 4101 tetrol in order to prepare more than 95% esterified V and 50% esterified diazirine benzoate esters IV. The acid II (76 grams) was dissolved in 50 mL DCM (all absorbed by the powder) in a 0.25 L tared and dried flask with addition of 25 mL of thionyl chloride (SOCl$_2$), followed by 3×12 mL of SOCl$_2$ added every hour over a duration of 3 hours. At the end of addition, a suspension was observed so it was left to stir at 35° C. overnight, thereafter resulting in a clear yellow solution. This solution was subjected to evaporation to remove volatile components, leaving behind 84 grams of yellow oil (constant weight of more than 99% yield).

Step (iii)—Preparation of Diazirine 1:2 Benzoate Ester V:

Capa 4101 tetrol 1 kDa, IV, (58.8 grams) was suspended (not dissolved) in 200 mL anhydrous diethyl ether (Et2O). 30.1 grams of the prepared acyl chloride III was added dropwise while stirring, and the mixture was left to stir overnight. On the next day, 10 mL of anhydrous pyridine was added and left to stir for 6 hours. The product V was extracted from the reaction mixture by adding, in sequence, aqueous 1 M HCl, then aqueous 10% NaHCO$_3$, then brine, then water, dried in vacuum and then freeze-dried (79.5 grams, 94.8% yield).

Step (iv)—Preparation of Diazirine 1:4 Benzoate Ester VI:

43.0 grams of IV was suspended in 200 mL of anhydrous Et2O, 53.9 gram of freshly prepared acyl chloride III was added dropwise while stirring, followed thereafter by 20 mL of anhydrous pyridine. The reaction mixture was stirred overnight. The mixture was dissolved in ethyl acetate (EtOAc), and treated with aqueous 1 M HCl, and then 10% aqueous NaHCO$_3$, then brine, and then dried on Na$_2$SO$_4$. The resultant yellow solution was left on a rotary evaporator till the product reaches a constant weight, leaving behind a yellow oil VI (74.3 grams, 93% yield).

Step (v)—Preparation of Antithrombotic Bioadhesive Formulation VII:

V was dissolved in acetone at 20% w/v followed by addition of sebacic acid (weight ratio of sebacic acid:V is 1:10). The mixture was then vortexed and subsequently evaporated to yield a homogeneous liquid.

Example 8: Mechanical Evaluation of Photo-Activated Crosslinked Bioadhesives V, VI and VII Using Low Intensity UVA Irradiation The rheometry analysis of viscoelasticity (G', storage modulus and G", loss modulus) as a function of UV irradiation was used to evaluate the crosslinking kinetics of V, VI, and VII. Each of these bioadhesives was applied as a liquid formulation, which then undergoes crosslinking to form a rubbery elastic bioadhesive upon UVA irradiation. This characteristic is important where a tissue bioadhesive is to be used as a sealant to prevent fluid leakage from artery and lungs. After crosslinking, the bioadhesive layer should possess a modulus that matches the treated tissue. In terms of mechanical characteristics, soft tissues exhibit moduli in the range of 10 kPa to 400 kPa. FIG. 1C shows the formation of diazoalkyl functional groups from the diazirine, and the depletion of diazirine groups from neat PCLT-D70 (liquid) ten seconds after exposure to low intensity UVA irradiation (1 J·cm$^{-2}$ at 365 nm) via a Fourier-Transform Infrared (FTIR) spectrum, as one example to demonstrate successful crosslinking.

Figure 5A:
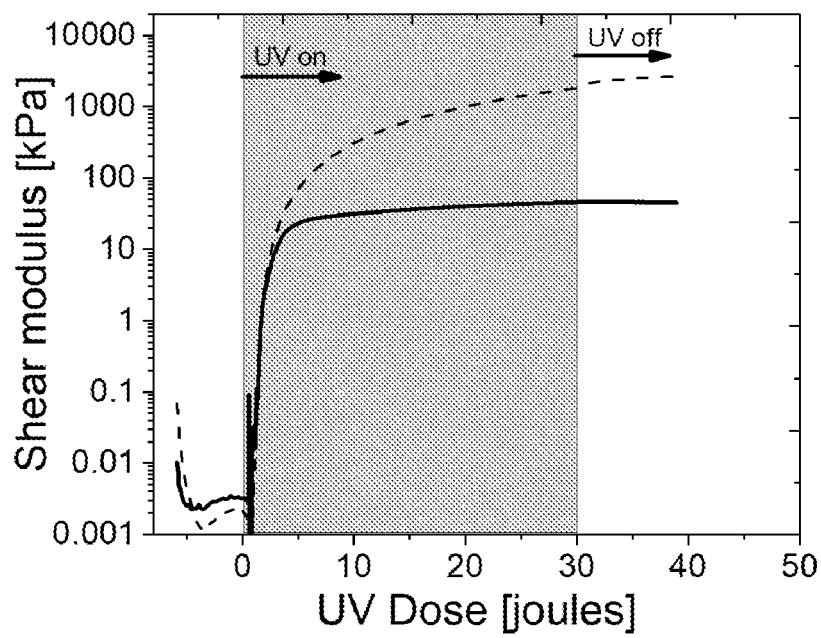
FIG. 5A shows the photocuring properties of diazirine benzoates V and VI derived from tetrol Capa 4101 (also see scheme 5 in example 7). The solid line and broken line represent for V and VI, respectively.
Figure 5B:
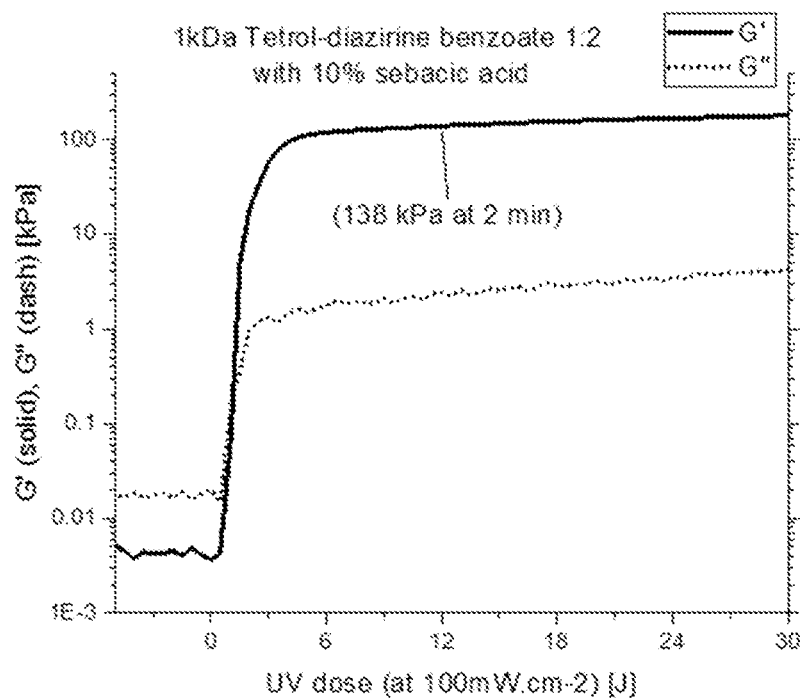
FIG. 5B shows the photocuring properties of diazirine benzoate VII derived from tetrol Capa 4101 (also refer to step (v) in example 7).
Figure 6:
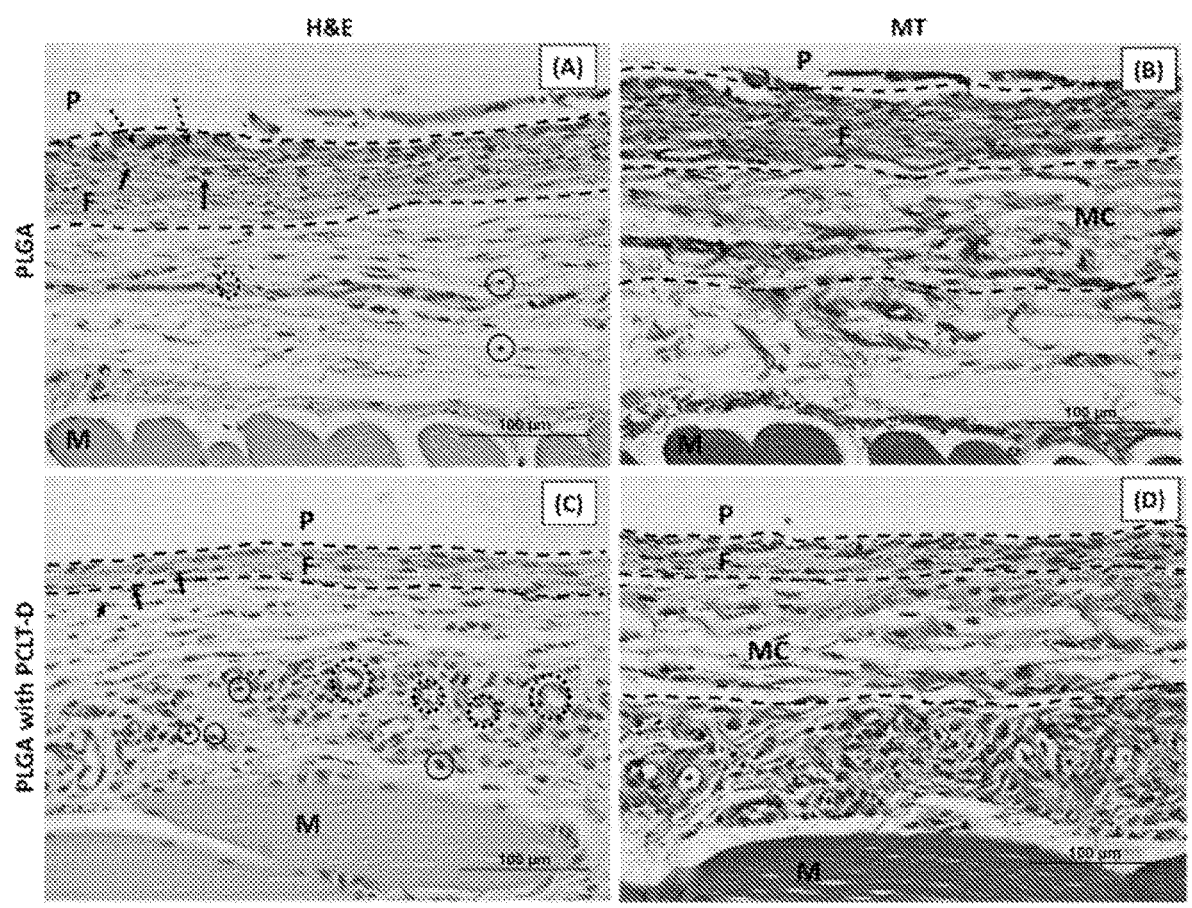
FIG. 6A shows the histology analysis after 7 days of subcutaneous implantation, by haemotoxylin and eosin (H&E) staining. Medical grade poly(lactic-co-glycolic acid) (PLGA) was used as a control. The scale bar represents 100 μm. The annotation of histology images is as follows: P—polymer; F—fibrous tissue; M—muscle tissue; MC—mature collagen (cross-sectional layers are separated with dashed lines). Dashed arrows point to macrophages while full line arrows point to polymorphonuclear cells. Dashed circles indicate neovascularization while full circles indicate lymphocyte cells.
FIG. 6B shows the histology analysis after 7 days of subcutaneous implantation by Masson's trichrome (MT) staining. Medical grade poly(lactic-co-glycolic acid) (PLGA) was used as a control. The scale bar represents 100 μm. The annotation of histology images is as follows: P—polymer; F—fibrous tissue; M—muscle tissue; MC—mature collagen (cross-sectional layers are separated with dashed lines). Dashed arrows point to macrophages while full line arrows point to fibroblasts. Dashed circles indicate neovascularization while full circles indicate lymphocyte cells.
FIG. 6C shows the histology analysis after 7 days of subcutaneous implantation by haemotoxylin and eosin (H&E) staining. PLGA patches with PCLT-D crosslinked and adhered to subcutaneous tissue by UV light were used. The scale bar represents 100 μm. The annotation of histology images is as follows: P—polymer; F—fibrous tissue; M—muscle tissue; MC—mature collagen (cross-sectional layers are separated with dashed lines). Dashed arrows point to macrophages while full line arrows point to fibroblasts. Dashed circles indicate neovascularization while full circles indicate lymphocyte cells.
FIG. 6D shows the histology analysis after 7 days of subcutaneous implantation by Masson's trichrome (MT) staining. PLGA patches with PCLT-D crosslinked and adhered to subcutaneous tissue by UV light were used. The scale bar represents 100 μm. The annotation of histology images is as follows: P—polymer; F—fibrous tissue; M—muscle tissue; MC—mature collagen (cross-sectional layers are separated with dashed lines). Dashed arrows point to macrophages while full line arrows point to fibroblasts. Dashed circles indicate neovascularization while full circles indicate lymphocyte cells.

FIGS. 5A and 5B show the joule dependence of G' and G" on UVA activation. All formulations crosslinked rapidly after UVA activation and the G' values attained were in excess of 40 kPa. A significantly higher G' of 2 MPa for VI was recorded after 20 J of UVA activation. In terms of biomaterial performance and tissue response, the bioadhesive formulation should demonstrate versatility in terms of control over mechanical properties. The rheological profile of the present adhesive is not only dependent on diazirine conjugation percentage but the crosslinking density, the latter of which also depends on the UVA dose. For example, V, VI, and VII have tunable G' values in desirable ranges required to match tissue mechanical properties by applying lower UVA doses. All formulations demonstrated liquid-like properties (G">G') before UVA activation and transitioned to an elastic biorubber after UVA activation. Liquid bioadhesive formulations conform to the surface of tissues and materials which they are applied to.

The bioadhesives can be applied as liquids and cured into an elastic bioadhesive biorubber in less than 30 seconds, for tissue bonding and sealant applications, for example, in the areas of cosmetics, fragrances, immobilization of medical devices to soft tissues, and replacement of mechanical fixation technologies (e.g. sutures, staples). The UVA dose determines the mechanical properties, which allows mimicking of the tissue substrates, preventing stress-strain mismatch and premature delamination.

Example 9: In Vivo Evaluation—Pre-Clinical In Vivo Immunological Response to Polycaprolactone Triol-G-Diazirine Polycaprolactone triol-diazirine, PCLT-D, belongs to the family of polycaprolactone biomaterials that have relatively slow resorbable kinetics, which can range from 6 months to 4 years, depending on their polymer (or copolymer) composition. As the polycaprolactone bioadhesives disclosed herein may be porous, their resorbable kinetics are expected to be better, thereby shortening resorption to week(s) instead of month(s).

PCLT-D formulation and controls were implanted subcutaneously into 10-weeks old Wistar female rats (300±50 grams) purchased from InVivos Pte. Ltd. (Singapore). All experiments were performed with the approval of the Nanyang Technological University Animal Care and Use Committee (IACUC; Protocol: ARF-SBS/NIE-A0301). Four full-thickness wounds (1.5 cm long and 0.5 cm deep) were made on the dorsum of each rat exposing the muscle tissue. Liquid bioadhesive formulations were first applied by spatula onto poly(lactic-co-glycolic acid) (PLGA) patches (diameter=6 mm; thickness=0.1 mm) and implanted directly on exposed muscle tissue (PLGA patches without bioadhesives were used as control). Bioadhesive patches were crosslinked using UVA light, with 365 nm UV filter at about 100 mW·cm$^{-2}$ for 1 min: 6 J·cm$^{-2}$). On the 7th day post-wounding, the animals were sacrificed and the dissected samples of skin with epidermal and dermal suture implants as well as internal implant material were fixed and stained with H&E (haemotoxylin and eosin) and MT (Masson's trichrome). All sections were evaluated and graded by a board-certified pathologist. FIG. 6A to 6D show the staining results.

FIG. 6A to 6D display the cured polycaprolactone bioadhesive and PLGA control. Subcutaneous implants were surrounded by mononuclear cells (macrophages, lymphocytes and plasma cells), polymorphonuclear cells (mainly neutrophils), and a relatively low number of giant cells, fibrosis and neovascularization. The fibrosis is accompanied by edema and neovascularization. There is a slightly higher degree of neovascularization and fibrosis, lymphoplasmacytic infiltration, and lesser giant cell infiltration around implants of PCLT-D compared to PLGA controls. The amount of collagen (stained blue in MT assay) per tissue area of implant-tissue interface in both PCLT-D and PLGA controls are similar. Histological analyses using H&E stains showed slight increase in mononuclear cell infiltration at the implant-tissue interface in the PCLT-D compared to PLGA controls. These consist of lymphocytes and plasma cells which are seen in chronic phase of inflammation as part of normal immune response. The fewer giant cells in PCLT-D suggest a lesser degree of foreign body reaction at the implant site compared to PLGA controls. Fibrosis and neovascularization, which are part of normal healing response, suggest a favourable environment for tissue regeneration at the implant-tissue interface of PCLT-D. Newly formed collagen (fibrosis area) analysed with MT staining indicate similar amount of collagen deposition per tissue area for pure PLGA and PCLT-D bioadhesive.

Example 10: Antithrombotic Properties of Present Polycaprolactone Triol-Diazirine with Sebacic Acid Antithrombotic surfaces are important consideration for bioadhesives designed for vascular (e.g. anastomosis) and cardiovascular pathologies (e.g. ventricular or atrial septal defect). Current bioadhesive films in contact with blood evoke the adsorption of fibrin (from plasma fibrinogen) which initiates thrombosis and can lead to blood clots. Naturally, the surface characteristics have a role in overall hemocompatibility of investigated biomaterials. Platelet morphological changes are one of the most common criterion for qualitative assessment of platelet activation.

Figure 7:
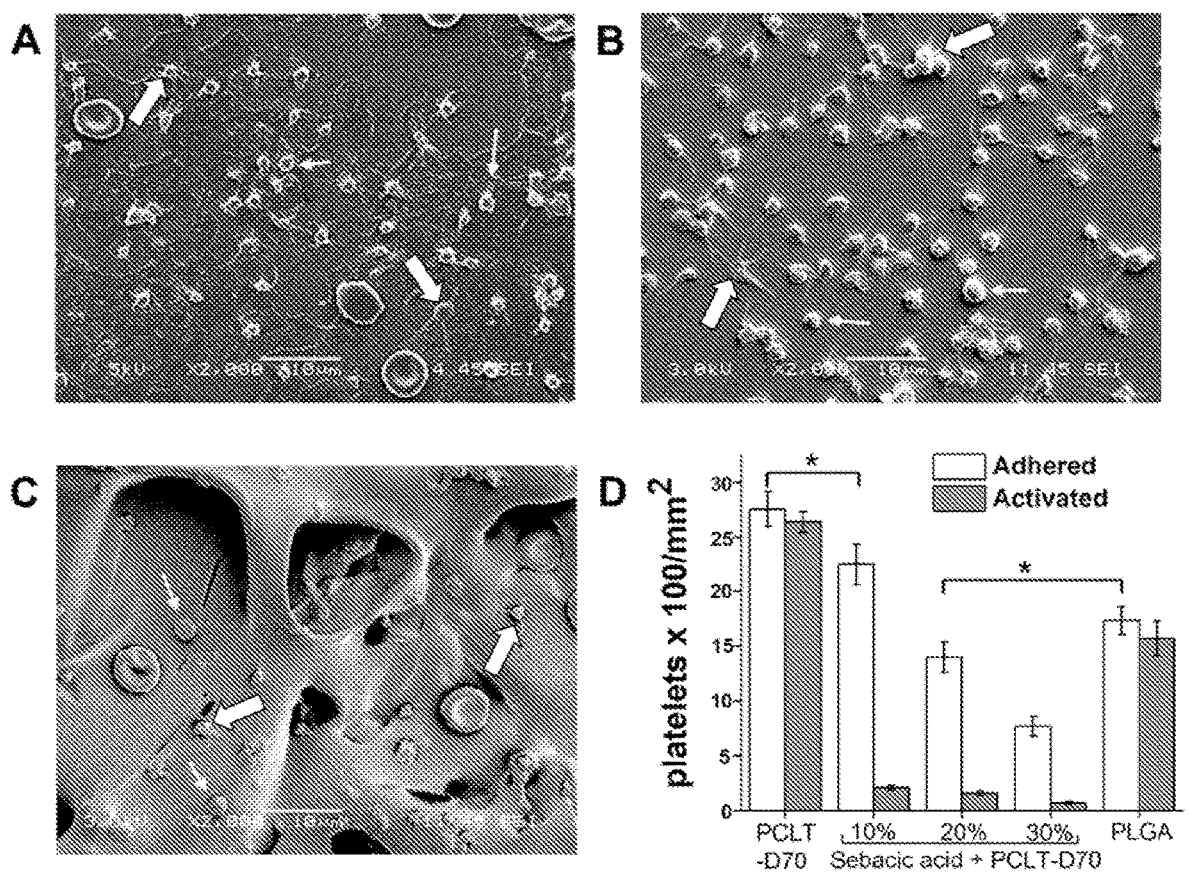
FIG. 7A shows the platelet adhesion test results using human blood on a PLGA control.
FIG. 7B shows the platelet adhesion test results using human blood on PCLT-D.
FIG. 7C shows the platelet adhesion test results using human blood on PCLT-D with sebacic acid (30%).
FIG. 7D shows a plot of the adhered and activated platelets on the surface of various bioadhesives. The "*" refers to a statistical significance of $p<0.005$.

Polycaprolactone triol-diazirine composites of the present disclosure were exposed to human blood and the results were compared to PLGA coatings used as control (FIG. 7A to 7D). Inactivated platelets were identified by their spherical morphology and often treated as in "resting stage" (full arrows). Activated platelets, characterized by the appearance of multiple pseudopodia (dotted arrows), were also detected on both control and bioadhesive surfaces. The number of platelets on the sample surfaces was quantified and results are shown in FIG. 7A to FIG. 7D. Gradual reduction of platelet adhesion and activation was observed on UV crosslinked composite with increasing concentration of sebacic acid (10%-30%, w/w). Sebacic acid serves as a biocompatible anti-thrombogenetic additive, wherein the hydrophobic property of polycaprolactone triol-diazirine allows its inclusion even though it could not be incorporated into water-based tissue adhesives. Quantitative analysis was performed to evaluate the total number of adhered and activated platelets per surface area and the results demonstrated that the number of adhered platelets was significantly reduced with increase in sebacic acid concentration (FIG. 7D). As an acid, it generates an anionic surface that prevents platelet adhesion and activation.

This example demonstrates that the present bioadhesive formulation has antithrombotic properties, as evaluated against human blood. The bioadhesive material properties combined with anti-thrombogenic surfaces allows the potential for therapies to address unmet clinical needs in the areas of cardiovascular and vascular pathologies (e.g. ventricular or atrial septal defects).

Example 11: Anastomosis Sealants of Blood Vessels

Anastomosis, the joining of two blood vessels, requires precise placement of sutures through the two blood vessels that need to be mended. The technique is technically challenging and requires a long learning curve through practice on cadavers, in vivo animal sacrifices, or both. The suturing practice of today has nearly been the same for 100 years. No notable advances have been made to address the complications that can arise, including long-term failure from scar tissue (intimal hyperplasia) or foreign body reactions to suture materials. Furthermore, blood vessels smaller than 1 mm joined together by sutures are unreliable, as they tend to fracture.

Figure 8:
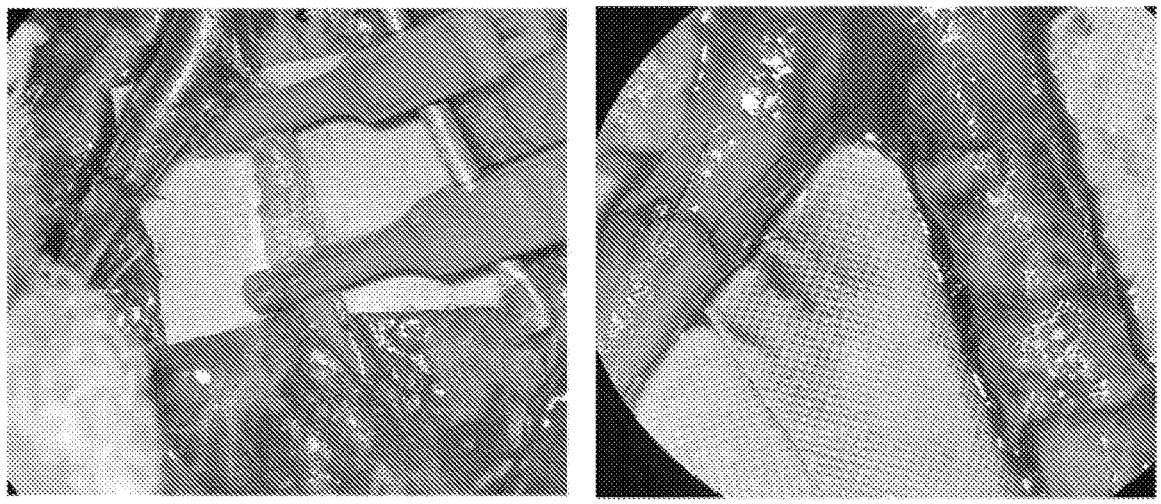
FIG. 8A shows a PCLT-D patch (yellow color) applied to a spliced iliac artery, with suture control. The left image shows the complete anastomosis construct while the right image shows upon harvesting after 7 days.
FIG. 8B shows the histopathology image of the half-moon splice. The scale bar represents 2 mm. Both half-moon and full-moon splices repaired by PCLT-D patch displayed patency of post operative (1 hour after application) and at sacrifice (7 days after application). Similar histopathology was observed between sutured and PCLT-D patch anastomosis.
FIG. 8C shows the histopathology image of the full-moon splice. The scale bar represents 2 mm. Both half-moon and full-moon splices repaired by PCLT-D patch displayed patency of post operative (1 hour after application) and at sacrifice (7 days after application). Similar histopathology was observed between sutured and PCLT-D patch anastomosis.
Figure 8:
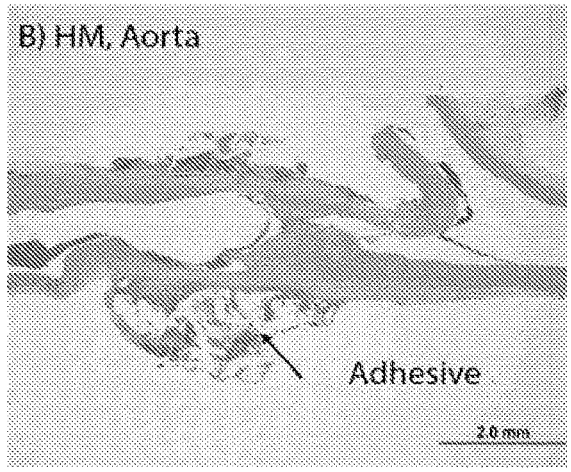
Figure 8:
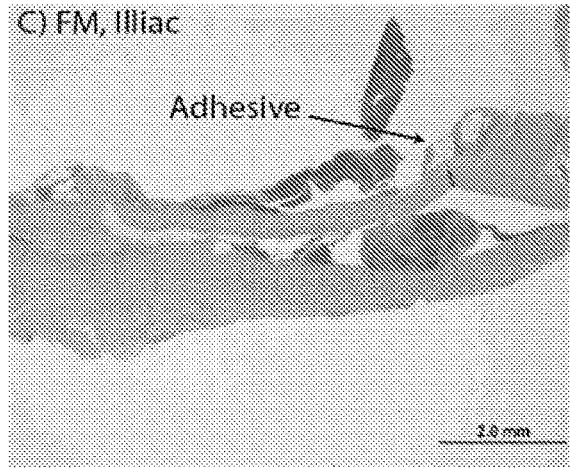

Pre-clinical trial to assess the ability of the present polycaprolactone triol-diazirine (PCLT-D) to anastomose a spliced artery so as to reduce dependency on suture. White New Zealand rabbits were anaesthetized, and the aorta and iliac arteries exposed. Iliac arteries were clipped both at dorsal and proximal ends, and spliced [half way; half-moon (HM) and completely full-moon (FM)]. The spliced arteries were stitched at 4 positions. A primer layer 95% PTCL-D was brushed and photocured with 5 J of UVA light. A polymer mesh was then fixed with a single stitch with iliac artery. A coat of PCLT-D was applied and photocured with 10 J of energy. The polymer mesh was rolled onto the cured adhesive followed by one more coat of PCLT-D. The PCLT-D was photocured with 10 J reinforcing the polymer mesh between the two adhesive layers, thereby reinforcing the adhesive matrix. Similar procedure was followed circumferentially by flipping the clips. Once PCLT-D together with the polymer mesh composite was photocured, it was allowed to rest before unclipping and allowing blood to flow. For control, the left iliac artery was spliced and sutured with 8 to 10 stitches. The live animal was harvested after 7 days and blind histopathological assessment was done by an external pathologist. FIG. 8A shows the representative digital image after anastomosis and 7 days post-application.

Anastomosis of 5 rabbits were done, two HM on aorta and 3 on iliac artery. All the rabbits survived the surgery. Upon unclipping, only 1 rabbit observed bleeding which was halted by irradiating the matrix with 5 J of UVA. At the end of 7 days, 4 out of 5 rabbit arteries were patent. Based on histopathological assessment (FIGS. 8B and 8C), HM anastomosed aorta has moderate inflammation and fibrosis. There is no luminal thrombosis observed to suggest disruption in lumen patency. HM and FM iliac arteries display similar response for the left (suture control) and right iliac (PCLT-D) with mild to moderate inflammation. The harvested artery was directly added to formalin without flushing out the residual blood leading to luminal thrombosis. Vessel lumen lining at the site of anastomosis, for all samples, appeared to be covered by tunica intima cells, an evidence of vessel re-endothelialization.

The present bioadhesives have been demonstrated and developed to adhere to wet tissues and withstand physiological blood pressure, with the additional capability of anti-thrombosis surfaces and sustained local drug delivery. The latter is demonstrated in the next example.

Example 12: Stress-Activated Local Anaesthesia to Surgical Tissues

Local anaesthetics (e.g. bupivacaine) are indispensable in providing patient comfort during and after most surgical procedures, but systemic toxicity through overdose is a potential risk. Current syringe injection of local anaesthetic limits pain relief to only a few hours, thus requiring systemic anaesthetics (e.g. opiates, non-steroidal anti-inflammatory drug) which may produce adverse side effects. Previous attempts have extended release to a few days, but these formulations suffered from static, pre-programmed release kinetics and possible migration. Patients therefore suffer from pain and discomfort as no host feedback is designed into the extended anaesthetic release formulation. The porosity of polycaprolactone triol-diazirine (PCLT-D) acts as a sponge that absorbs and expels fluids upon strain, which serves as a method for stress-activated drug delivery.

Bupivacaine anaesthetic drug was incorporated into the present PCLT-D bioadhesive through ultrasonication. The gastrocnemius muscle (female Wister Rat) was exposed and 25 mg of control or bioadhesive was photocured directly on the incision using an effective UV dose of 20 J. For control, bupivacaine was delivered via saline (set A in FIG. 9A). Neat PCLT-D (set C in FIG. 9A) and 10% w/w Bupivacaine:PCLT-D70 (set B in FIG. 9A) formed the experiment group. The wound was closed with an uninterrupted square stitch. Post-operative locomotor analysis was performed in a 1 m wide box to assess the pain against the healing cycle with respect to the bioadhesives used. After 7 days, the rats were sacrificed and blind histopathological assessment was performed for inflammatory and tissue regeneration (n=5).

Figure 9:
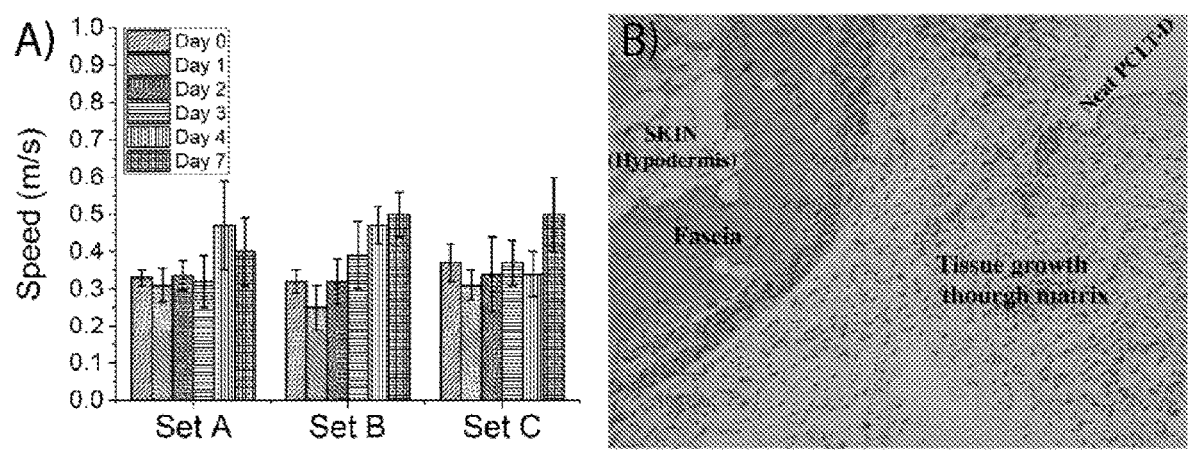
FIG. 9A shows the locomotor behavior for formulations A, B, and C over 7 days. Photocured PCLT-D (set B and set C) was non-inferior to set A (bupivacaine control).
FIG. 9B shows the tissue regeneration within the porous photocured PCLT-D matrix. The scale bar represents 100 μm.

The locomotor studies were done by measuring the speed of rat over a distance of one 1 m on day 0 (after operation), 1, 2, 3, 4 and 7. As seen in FIG. 9A, the average velocity of each rat showed similar trend regardless of formulation. Compared to sets A and C, set B displayed linear increases in the velocity continuously till day 4. Based on statistical analysis, the velocity of each group was not statistically different. The performance of PCLT-D was non-inferior to bupivacaine control. Based on the blind histopathological report, cured bioadhesives (sets B and C) did not show any inverse response in comparison to bupivacaine saline (set A) samples. There was no indication of UV induced necrosis or inflammation. 9 out of 12 operation sites of set C showed granulation tissue formation when compared to 6 out of 12 operated sites of set B and 5 out of 12 operated sites of set C. Similarly, 8 out of 12 for set A, 9 out of 12 for set B and 10 out of 12 for set C operational sites has an inflammation score of 0 or 1. Based on histological analysis (e.g. see FIG. 9B), tissue regeneration in set C was the most complete, with over 50% of resorbed photocured adhesive displaying new tissue growth.

Based on the results shown in FIGS. 9A and 9B, the present bioadhesives maintained adhesion to wet tissues while simultaneously acting as a hydrophobic drug delivery depot with over 50% resorbance of polycaprolactone matrix within 7 days. Conventionally, commercial bioadhesives are not capable or may have difficulty incorporating hydrophobic drugs for controlled drug delivery.

Example 13: Commercial and Potential Applications

Polycaprolactone (PCLT) precursors (star-shaped PCLT with molar mass of less than 3000 Da) may exist as liquid under 50° C. with viscosities under 1 Pa·s. Hence, the PCLT precursors require no dilution in aqueous or organic solvents (i.e. in their neat form) and can be easily applied by syringe or other liquid applicators. The PCLT precursors can be synthesized into PCLT bioadhesives in a one-pot synthetic method with grafting of suitable carbene precursor (i.e. diazirine). The synthetic methodology allows a scalable production with reasonable yield, from laboratory batch production to continuous reactor-scale production.

The resultant PCLT bioadhesives are hydrophobic materials that prevent water infiltration into the polymer matrix. This allows long-term shelf storage of 12 months or greater, as hydrolysis of the carbene precursor is prevented. The PCLT bioadhesives also act as water impenetrable sealant and coatings on both dry and hydrated surfaces. They can also be modified to be porous or non-porous by suitable changes in pore-forming additives.

The present bioadhesive formulation can be used with hygroscopic additives. That is to say, the resultant PCLT bioadhesives can be PCLT hygroscopic composite adhesives (PCLT-HYGRO). Such composites allow temporary reduction of adhesive fouling and surface water-hydration. Hydrated surfaces may be an obstacle in creating highly crosslinked substrates for non-aqueous liquid adhesives. Upon contact with wet substrates, PCLT-HYGRO advantageously reduces the amount of surface water-hydration after 10 to 300 seconds of contact. Subsequent curing allows increased interfacial bond strengths.

The low molecular weight polycaprolactone (PCLT) precursors and PCLT bioadhesives are able to dissolve linear and branched PCLT oligomers (2 kDa to 10 kDa) and PCLT polymers (more than 10 kDa) to form PCLT adhesive composites (PCLT-COMP). This allows a high degree of flexibility in pre-cured material properties and post-cured adhesive material properties. Viscoelastic material properties can be flexibly tuned.

Accordingly, the PCLT-HYGRO, PCLT-COMP, and a combination thereof, have enhanced rheological properties for unmet sealant, coating, and medical applications. For example, polycaprolactone triol (molar mass 2000 Da, Perstorp CAPA 3201) grafted with 1 to 3 molar equivalents of diazirine is a liquid at 50° C. (viscosity less than 1 Pa·s) but gels on contact with substrates at not more than 40° C. Thus, the present PCLT bioadhesive formulation is easily applied (even at 50° C. or more) using a syringe, brush, spray, etc., and yet remains stationary on contact with the tissue substrate at temperatures below 40° C.

The present bioadhesive formulation also allows for easy removal from the substrate when in its pre-cured state (e.g. by mechanical peeling or dissolving in organic solvents). Upon curing, the crosslinking matrix is able to adhere to the tissue surface it is applied on to fix or seal the tissue opening (e.g. wound). Advantageously, the cured matrix, being hydrophobic, prevents water from penetrating into the wound.

The curing can be established through various approaches, without being limited to, UVA irradiation (1 mW·cm$^{-2}$ to 1000 mW·cm$^{-2}$), application of voltage (2 V to 50 V) or an electrical current (1 mA to 100 mA). Subcutaneous tissue curing can be established through near infrared irradiation (1 mW·cm$^{-2}$ to 1000 W·cm$^{-2}$) using two-photon absorption.

The methods of forming the present bioadhesives are economically viable as low cost polycaprolactone precursors (e.g. triols and tetrols) are economically available at food grade purity. Such precursor may cost less than 10 USD per kg.

Moreover, any thermoplastic polycaprolactone with a melting point of less than 90° C. can be converted into moldable thermoplastic polycaprolactones that can be photoset (light cured) or thermoset (thermal curing above 110° C.).

The degree of curing is not compromised as multi-arm (e.g. from 3 to 6 arms) polycaprolactone precursors (star-shaped PCLT with molar mass less than 3000 Da) functionalized with 17% to 100% (based on, for example, pendant —OH groups) carbene precursor, e.g. diazrine, are already liquids under 50° C. with viscosities under 1 Pa·s. The PCLT precursors require no dilution in aqueous or organic solvents (in their neat form), and they can be easily applied by liquid applicators without compromising the crosslinking.

Advantageously, the stimulant (UVA intensity, joules dose, wavelength activation, etc.) can be controlled to tune the ratio of carbene/diazoalkyl functional groups. For example, activation of diazirine functional groups into carbene/diazoalkyl functional groups can be achieved using two-photon absorption.

The bioadhesives disclosed herein have commercial applications in the market of medical plastics for surgical instruments. The market for such materials, in America, is expected to reach 645 million pounds by year 2020.

Another potential use of the present bioadhesives is its application as a minimally invasive surgery (MIS) device, particularly as a bioadhesive for use in cardiothoracic surgery procedures. For example, the present bioadhesive may be used to seal hydrated tissues. The global market for MIS devices, which include the bioadhesives as disclosed herein, is estimated to reach $21.5 billion by 2019.

While the invention has been particularly shown and described with reference to specific embodiments, it should be understood by those skilled in the art that various changes in form and detail may be made therein without departing from the spirit and scope of the invention as defined by the appended claims. The scope of the invention is thus indicated by the appended claims and all changes which come within the meaning and range of equivalency of the claims are therefore intended to be embraced.

The invention claimed is:

1. A bioadhesive formulation comprising a polycaprolactone dendrimer having a dendrimer core and a plurality of polycaprolactone chains extending from the dendrimer core, wherein at least one of the polycaprolactone chains has an end which is covalently attached with a diazirine, and wherein the diazirine converts to a carbene and/or a diazoalkyl when a stimulant is applied to the bioadhesive formulation.

2. The bioadhesive formulation according to claim 1, wherein each of the polycaprolactone chains comprises one or more repeating units of:

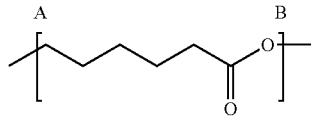

wherein part A of each repeating unit extends away from the dendrimer core and part B of each repeating unit extends toward the dendrimer core, and wherein in the at least one polycaprolactone chain having the end which is covalently attached with the diazirine, part A of the repeating unit arranged furthest away from the dendrimer core forms the end at which the diazirine is covalently attached to the at least one polycaprolactone chain.

3. The bioadhesive formulation according to claim 2, wherein part A of the repeating unit arranged furthest away from the dendrimer core forms the end at which there is an oxygen for forming an ether linkage, an ester linkage, or an anhydride linkage, with the diazirine.

4. The bioadhesive formulation according to claim 3, wherein the diazirine is represented by the formula:

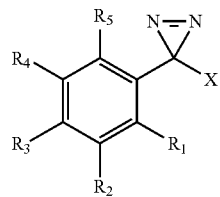

wherein at least one of $R_1$ to $R_5$ is hydrogen, —$C_{1-12}$ alkyl- which is unsubstituted or substituted with one or more halogens, or —$R_6C(=O)$—;
wherein the —$C_{1-12}$ alkyl- in at least one of $R_1$ to $R_5$ is covalently attached to the oxygen to form an ether linkage or an ester linkage with the polycaprolactone chain;
wherein the —$R_6C(=O)$— in at least one of $R_1$ to $R_5$ is covalently attached to the oxygen to form an ester linkage or an anhydride linkage with the polycaprolactone chain;
wherein $R_6$ is a bond or —$C_{1-12}$ alkyl- which is unsubstituted or substituted with one or more halogens; and
wherein X is hydrogen, halogen or —$C_{1-12}$ alkyl substituted with one or more halogens.

5. The bioadhesive formulation according to claim 1, wherein the diazirine comprises:

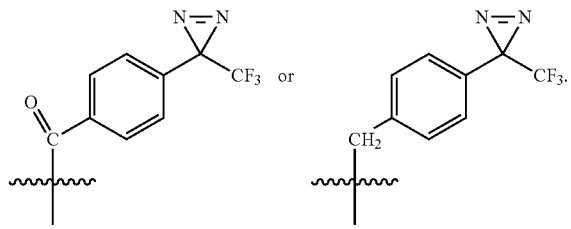 [SMILES: *C(=O)c1ccc(C2(C(F)(F)F)N=N2)cc1 ; *Cc1ccc(C2(C(F)(F)F)N=N2)cc1]

6. The bioadhesive formulation according to claim 1, wherein the bioadhesive formulation further comprises a hygroscopic additive, an antithrombotic agent, and/or an anaesthetic agent.

7. The bioadhesive formulation according to claim 6, wherein the hygroscopic additive comprises anhydrous citric acid, anhydrous ethanol, anhydrous magnesium sulfate, and/or hydroxyapatite.

8. The bioadhesive formulation according to claim 6, wherein:
the antithrombotic agent comprises sebacic acid; or
the anaesthetic agent comprises bupivacaine.

9. The bioadhesive formulation according to claim 1, wherein the bioadhesive formulation is in the form of a liquid formulation, wherein the liquid formulation becomes a cured bioadhesive when the stimulant is applied to the bioadhesive formulation.

10. The bioadhesive formulation according to claim 1, wherein the stimulant comprises (i) electromagnetic radiation having one or more wavelengths from 315 nm to 1400 nm, (ii) electromagnetic radiation having one or more intensities in the range of 1 mW·cm$^{-2}$ to 1000 mW·cm$^{-2}$, (iii) a current in the range of 1 mA to 100 mA and/or (iv) a voltage in the range of ±50 V.

* * * * *